(12) United States Patent
Komorowski et al.

(10) Patent No.: US 10,183,049 B2
(45) Date of Patent: Jan. 22, 2019

(54) MACA COMPOSITIONS AND METHODS OF USE

(71) Applicant: NUTRITION 21, LLC, Purchase, NY (US)

(72) Inventors: James R. Komorowski, Trumbull, CT (US); Sara Perez Ojalvo, New York, NY (US)

(73) Assignee: NUTRITION 21, LLC, Purchase, NY (US)

( * ) Notice: Subject to any disclaimer, the term of this patent is extended or adjusted under 35 U.S.C. 154(b) by 0 days.

(21) Appl. No.: 15/785,170

(22) Filed: Oct. 16, 2017

(65) Prior Publication Data

US 2018/0110818 A1     Apr. 26, 2018

Related U.S. Application Data

(60) Provisional application No. 62/411,977, filed on Oct. 24, 2016.

(51) Int. Cl.
| | | |
|---|---|---|
| *A61K 36/31* | (2006.01) | |
| *A61K 36/00* | (2006.01) | |
| *A23L 2/00* | (2006.01) | |
| *A61K 9/00* | (2006.01) | |

(52) U.S. Cl.
CPC ............... *A61K 36/31* (2013.01); *A23L 2/00* (2013.01); *A61K 9/00* (2013.01)

(58) Field of Classification Search
None
See application file for complete search history.

(56) References Cited

U.S. PATENT DOCUMENTS

| | | | |
|---|---|---|---|
| 5,942,220 A | 8/1999 | Warren et al. | |
| 2004/0137131 A1* | 7/2004 | Bobrowski | A23K 20/147 426/615 |
| 2006/0147600 A1 | 7/2006 | Gonzales et al. | |
| 2009/0280203 A1* | 11/2009 | Gonzales Rengifo | A61K 36/28 424/773 |
| 2013/0177513 A1 | 7/2013 | Saunois et al. | |
| 2018/0110817 A1 | 4/2018 | Komorowski et al. | |

FOREIGN PATENT DOCUMENTS

EP             2481300         8/2012

OTHER PUBLICATIONS

The website document entitled "The MACA Team" (available at https://www.themacateam.com/black-maca-how-its-different-and-why-to-try-it). (Year: 2014).*
Gonzales et al. (2010) Forsch. Komplementmed. 17: 137-143. (Year: 2010).*
Gonzalez et al. (2009) Forsch. Komplementmed. 16: 373-380. (Year: 2009).*
Rubio et al. (2006) BMC Complementary and Alternative Med. 6: 23 (7 pages) (Year: 2006).*
Benson et al., "Antioxidant, anti-inflammatory, anti-apoptotic, and skin regenerative properties of an Aloe vera-based extract of *Nerium oleander* leaves (NAE-8(®)" Clin Cosmet Investig Dermatol. 2015; 8: pp. 239-248.
Benson et al., "West African *Sorghum Bicolor* Leaf Sheaths Have Anti-Inflammatory and Immune-Modulating Properties In Vitro,"J Med Food; 2013; 16(3): pp. 230-238.
Dini et al.,"Chemical composition of *Lepidium meyenii,*" Food Chemistry, 1994; 49: pp. 347-349.
Gasco et al., "Effect of chronic treatment with three varieties of *Lepidium meyenii* (Maca) on reproductive parameters and DNA quantification in adult male rats," Andrologia, 2007; 39: pp. 151-158.
Li et al.,"Glucosinolate Contents in Maca (*Lepidium Peruvianum Chacón*) Seeds, Sprouts, Mature Plants and Several Derived Commercial Products," Economic Botany, 2001; 55(2): pp. 255-262.
Muhammad et al., "Maca (*Lepidium meyenii*)," Encyclopedia of Dietary Supplements, 2005; 435-443.
Piacente et al., "Investigation of the Tuber Constituents of Maca (*Lepidium meyenii* Walp.)," J. Agric. Food Chem., 2002; 50: pp. 5621-5625.
Bai et al., "Flavonolignans and Other Constituents from *Lepidium meyenii* with Activities in Anti-inflammation and Human Cancer Cell Lines," Journal of Agriculture and Food Chemistry, 2015; 63(9): pp. 2458-2463.
Brooks et al., "Beneficial effects of *Lepidium meyenii* (Maca) on psychological symptoms and measures of sexual dysfunction in postmenopausal women are not related to estrogen or androgen content," Menopause: The Journal of the North American Menopause Society, 2008; 15(6): pp. 1157-1162.
Clément et al., "Effect of maca supplementation on bovine sperm quantity and quality followed over two spermatogenic cycles," Theriogenology, 2010; 74(2): pp. 173-183.
Clément et al., "Influence of colour type and previous cultivation on secondary metabolites in hypocotyls and leaves of maca (*lepidium meyenii* Walpers)," Journal of the Science of Food and Agriculture; 2010; 90(5): pp. 861-869.
International Search Report and Written Opinion issued in related Application No. PCT/US17/58166, dated May 8, 2018.
Meissner et al., "Hormone-Balancing Effect of Pre-Gelatinized Organic Maca (*Lepidium peruvianum* Chacon): (III) Clinical responses of early-postmenopausal women to Maca in double blind, randomized, Placebo-controlled, crossover configuration, outpatient study," International Journal of Biomedical Science, 2006; 2(4): pp. 375-394.
Zheng et al., "Effect of a lipidic extract from *Lepidium meyenii* on sexual behavior in mice and rats," Urology, 2000; 55(4): pp. 598-602.
Alzamora et al., "Effect of four ecotypes of *Lepidium peruvianum* Chacón on the production of nitric oxide in *vitro*," Rev. peru. biol. número especial, 2007; 13(3): pp. 215-217. (English Abstract included).
Bianchi, "Maca *Lepidium meyenii*," Boletín Latinoamericano y del Caribe de Plantas Medicinales y Aromáticas, 2003; 2(3): pp. 30-36.

(Continued)

*Primary Examiner* — Christopher R Tate
*Assistant Examiner* — Russell G Fiebig
(74) *Attorney, Agent, or Firm* — Porzio, Bromberg & Newman P.C.

(57) ABSTRACT

The present application is directed to composition comprising various maca extracts and the use of such compositions for treating certain diseases, disorders, and conditions.

8 Claims, 18 Drawing Sheets

(56) References Cited

OTHER PUBLICATIONS

Carrión et al., "Antioxidant Activity of Three Ecotypes of Maca (*Lepidium Meyenii Walp*) Treated With Gamma Radiation," Revista Peruana Química Ingenieria Quimica, 2009; 12(2): pp. 72-77. (English Abstract included).
Gasco et al., "Effect of chronic treatment with three varieties of Lepidium meyenii (Maca) on reproductive parameters and DNA quantification in adult male rats," Andrology, 2007; 39(4): pp. 151-8. (Abstract only).
Gasco, "Dose-response effect of red maca (*Lepidium meyenii*) on benign prostatic hyperplasia induced in by testosterone enanthate," Phytomedicine, 2007; 14: pp. 460-464. (Abstract only).
Gonzales et al., "Maca (*Lepidium meyenii* Walp), a review of its biological properties," Rev Peru Med Exp Salud Publica, 2014; 31(1): pp. 100-110. (abstract).
Gonzales et al., "Red maca (*Lepidium meyenii*) reduced prostate size in rats," Reproductive Biology and Endocrinology, 2005; 3(5): pp. 1-16.
Gonzales, "Effect of Black maca (*Lepidium meyenii*) on one spermatogenic cycle in rats," Andrologia, 2006; 38(5): pp. 166-72. (Abstract only).
Gonzales, "Ethnobiology and Ethnopharmacology of *Lepidium meyenii*(Maca), a Plant from the Peruvian Highlands," Evidence-Based Complementary and Alternative Medicine, 2012; Article ID 193496, 10 pages.
Meissner et al., "Peruvian Maca (*Lepidium peruvianum*): (II) Phytochemical Profiles of Four Prime Maca Phenotypes Grown in Two Geographically-Distant Locations," International Journal of Biomedical Science, 2016: 12(1): pp. 9-24.
Monteghirfo et al., "Characterization of three maca (*Lepidium peruvianum* G. Chacon) echotypes' total proteins by unidimensional y bidimensional electrophoresis," an Fac. Med., 2007; 68(4): pp. 301-306. (English Abstract included).
Ramírez, " Biotechnology and Secondary Metabolitos in *Lepidium peruvianum*Chacón. "MACA"," Thesis to apply for the Professional Title of Biologist, 2002. (English Abstract and machine translation of title page and Chapter I Summary).
SelvaBio Ltd., Triple Maca root Organic and Gelatinized. [online], 2012. Available in https://www.selvabio.com/gb/maca-root/1-triple-maca-root-organic-gelatinized-0784927218297.html.
Third Party Observations filed with WIPO in PCT/US2017/058166, dated Oct. 1, 2018.

\* cited by examiner

MACA COMPOSITIONS AND METHODS OF USE

INCORPORATION BY REFERENCE TO RELATED APPLICATIONS

This application claims priority to of U.S. Provisional Application No. 62/411,977 filed Oct. 24, 2016, the contents of which is incorporated by reference herein in its entirety.

BACKGROUND

The present disclosure relates to novel compositions of maca root (*Lepidium meyenii*, also called Peruvian *Ginseng*) and methods of using same. Such compositions may be used, for example, in improved methods of increasing libido, ameliorating sexual dysfunction caused by antidepressants, decreasing inflammation, increasing energy levels, increasing stamina, increasing athletic performance, improving memory, ameliorating discomfort related to menstruation, ameliorating the symptoms of hormonal imbalances, HIV/AIDS, cancer (including discomfort due to administration of chemotherapy to treat cancer), menopause, andropause, anemia, osteoporosis, and chronic fatigue syndrome, improving fertility, decreasing symptoms of tuberculosis, improving mood (for example, reducing depression), and increasing immune function.

More particularly, the present disclosure relates to the surprising and unexpected finding that particular combinations of maca root varieties are more effective than other maca root varieties, alone or in other combinations, at reducing inflammatory markers, such as cytokines, and thus may likely be more effective and/or provide more beneficial results to subjects ingesting the compositions disclosed herein than previous maca root containing products.

Maca is used as a food, similar to sweet potatoes, but also has a number of medicinal properties. Traditionally, maca is processed by boiling, baking, and drying the root, and then grinding the dried root material into powder. Various maca root powders are commercially available. Fresh maca roots have different colors due to genetic variations that result in different phytochemical profiles in the different maca phenotypes. The different genotypes, reflected in root color phenotype include yellow, red, purple, blue, black, and green. Yellow maca is the largest and sweetest-tasting, and are most commonly grown for food, while red and black maca are generally considered more medicinally potent, for example, to reduce inflammation.

Inflammation is part of the non-specific immune response that occurs in reaction to bodily injury. Cytokines, amongst other factors, are regulators of the inflammatory process. Cytokines are small, secreted proteins with a specific effect on the interactions and communications between cells. There are both pro-inflammatory cytokines and anti-inflammatory cytokines.

Interleukin 6 (IL-6), for example, has broad physiological effects, including both pro- and anti-inflammatory properties, depending on the biological context. IL-6 is implicated in numerous disease processes, including chronic inflammation, diabetes, and rheumatoid arthritis. While IL-6 is a promising target for clinical intervention, its complicated signal transduction pathway makes such intervention challenging.

Inflammation can also lead to sexual problems (or sexual dysfunction). These conditions are widespread and adversely affect mood, well-being, and interpersonal relationships. Most sexual problems relate to sexual desire (libido) in both females and males and male erectile dysfunction (ED). Current pharmacological interventions for the management of sexual problems include drugs, intrapenile therapies, and penile prosthesis implantation for males and hormonal therapy for females. Treatment of sexual problems in females is also problematic, with pharmacological treatments often resulting in severe, undesirable side-effects. Non-pharmacological treatments include vaginal electromyography biofeedback, pelvic floor physical therapy, cognitive behavioural therapy, transcutaneous electrical nerve stimulation, and vestibulectomy. Post-menopausal women may also suffer from decreased libido, in part due to falling estrogen and testosterone levels. Decreased libido remains a significant sexual problem in both males and females.

SUMMARY

This application is based in part on the surprising discovery that certain maca root blends provide an unexpected increase in the reduction of the anti-inflammatory response of cells. In some aspects, the maca root blends can be used to treat, ameliorate and/or prevent inflammatory responses. In some aspects, the maca root blends, disclosed herein, may be used to increase libido and or to treat, ameliorate, or prevent symptoms of sexual dysfunction. After considering this discussion, and particularly after reading the section entitled "Detailed Description" and the attached appendix (Appendix A, which is herein incorporated by reference in its entirety), one will understand how the features of the compositions and methods disclosed herein provide advantages over other known compositions and methods.

Embodiments disclosed herein relate to compositions that comprise, consist essentially of, or consist of a mix of one or more maca roots. Such compositions may be used to, for example, to reduce an individual's inflammatory response. In some aspects, the compositions include a maca root blend of one or more phenotypes (color) of maca root. In some aspects, the one or more maca root phenotypes are pulverized into a powder. In some aspects, the composition includes a macamide-macamene mixture. In some embodiments, the maca roots used in the maca compositions are selected based on their macamide and/or macamene content.

Other embodiments disclosed herein relate to the use of such compositions. These compositions are useful for, inter alia, increasing anti-inflammatory properties and decreasing inflammatory cytokine production, which will necessarily affect the many pathways that are affected by the anti-inflammatory pathway, including but not limited to increasing libido and reducing the effects of chronic inflammation. In some embodiments, the compositions disclosed herein may be useful for treating or enhancing sex drive in individuals undergoing menopause or other hormonal imbalances.

Some embodiments provide a method for increasing sex drive in individuals with hormonal imbalances. For example, a method may include administering an effective amount of a maca root blend to a subject. The subject's desire to engage in sexual activity may be increased relative to providing no maca root or other maca root blends.

In another aspect, the embodiments relate to methods of treating a subject with the compositions disclosed herein. The terms "subject," "patient" or "individual" as used herein refer to a vertebrate, preferably a mammal, more preferably a human. "Mammal" can refer to any animal classified as a mammal, including humans, domestic and farm animals, and zoo, sport, or pet animals, such as, for example, horses, sheep, cows, pigs, dogs, cats, etc. Preferably, the mammal is human.

In some embodiments, the composition includes black maca root, yellow maca root, red maca root, or any combination of the foregoing.

In some embodiments, a maca root blend comprises a combination of black and yellow maca. In some embodiments, a maca root blend comprises some combination of black and red maca. In some embodiments, a maca root blend comprises some combination of red and yellow maca. In some embodiments, a maca root blend is a one to one ratio of two maca root phenotypes. In some embodiments, a maca root blend is a two to one ratio of two maca root phenotypes. In some embodiments, a maca root blend is a four to one ratio of two maca root phenotypes.

Some embodiments are formulated as nutritional supplements. Such supplements may be formulated to be consumed daily. For example, the maca containing nutritional supplement may be formulated to deliver about 1 to about 40 grams of maca root per day per individual subject. This can occur in one, two, three or more doses during the day and can occur daily over a period of one, two, three or more days, or weeks, as well as longer periods as would be envisaged by the skilled artisan.

In some embodiments, the maca root is present at an effective dose. In some embodiments, the supplement is a solid. In some embodiments, the solid is a powder. In some embodiments, the supplement is a liquid. In some embodiments, the liquid is a concentrated formulation. In some embodiments, the supplement further comprises at least one of a sweetener and a flavoring agent.

Some embodiments provide a method of making a composition comprising a maca root blend and excipients. The method may include boiling, baking, and drying the maca root and combining with some amount of excipients.

Some embodiments provide a method of making a composition comprising a maca root blend and excipients. In some embodiments, the composition is further formulated for oral administration to a subject.

In some embodiments, the nutritional supplement further comprises a second agent. In some embodiments, the second agent is selected from a hormone, a non-steroidal anti-inflammatory agent, a vitamin, a mineral, and combinations of the foregoing.

Some embodiments provide compositions comprising an amount of black maca root and an amount of red maca root, wherein the amounts have a ratio of black maca root to red maca root, and the ratio is from about 1:1 to about 4:1. Some embodiments provide compositions comprising an amount of black maca root and an amount of red maca root, wherein the amounts have a ratio of black maca root to red maca root, and the ratio is from about 1:1 to about 4:1. Some embodiments provide compositions comprising an amount of black maca root and an amount of yellow maca root, wherein the amount have a ratio of black maca root to yellow maca root, and the ratio is from about 2:1 to 1:2.

Some embodiments provide methods of increasing libido in a subject in need thereof, comprising co-administering a composition comprising a synergistically effective amount of black maca root and red maca root to the subject. Some embodiments provide methods of increasing libido in a subject in need thereof, comprising co-administering a composition comprising a synergistically effective amount of black maca root and yellow maca root to the subject.

Some embodiments provide methods of decreasing cytokine activity in a subject in need thereof, comprising administering a composition comprising a synergistically effective amount of black maca root to red maca root to the subject, wherein the cytokine is selected from IL-1β, IL-6, IL-8, and combinations thereof. Some embodiments provide methods of decreasing cytokine activity in a subject in need thereof, comprising administering a composition comprising a synergistically effective amount of black maca root to yellow maca root to the subject, wherein the cytokine is selected from IL-1β, IL-6, IL-8, IP-10, IL-4, IFN-γ, and combinations thereof.

Some embodiments provide for use of compositions for improved treatment of sexual dysfunction in humans, the composition comprising a first amount of black maca root and a second amount of red maca root, the first and second amounts provided in a synergistic ratio. Some embodiments provide for use of compositions for improved treatment of sexual dysfunction in humans, the composition comprising a first amount of black maca root and a second amount of yellow maca root, the first and second amounts provided in a synergistic ratio.

Some embodiments provide compositions consisting essentially of an approximately 1:4 ratio of black to red maca root for use in treating sexual dysfunction. Some embodiments provide compositions comprising an amount of black maca root and an amount of yellow maca root, wherein the amounts have a ratio of black maca root to yellow maca root, and the ratio is about 1:1. Some embodiments provide compositions consisting essentially of an approximately 1:1 ratio of black to yellow maca root for use in treating sexual dysfunction.

Some embodiments provide improved methods of increasing libido. Some embodiments provide improved methods of ameliorating sexual dysfunction caused by antidepressants. Some embodiments provide improved methods of decreasing inflammation. In some embodiments, these methods comprise providing a composition comprising an effective amount of at least two of black maca root, yellow maca root, and red maca root. In some embodiments the ratio of two of the phenotypes is from about 1:1 to about 4:1.

Some embodiments provide improved methods of increasing energy levels. Some embodiments provide improved methods of increasing stamina. Some embodiments provide improved methods of increasing athletic performance. In some embodiments, these methods comprise providing a composition comprising an effective amount of at least two of black maca root, yellow maca root, and red maca root. In some embodiments the ratio of two of the phenotypes is from about 1:1 to about 4:1.

Some embodiments provide improved methods of improving memory. In some embodiments, these methods comprise providing a composition comprising an effective amount of at least two of black maca root, yellow maca root, and red maca root. In some embodiments the ratio of two of the phenotypes is from about 1:1 to about 4:1.

Some embodiments provide improved methods of ameliorating discomfort related to menstruation. Some embodiments provide improved methods of ameliorating the symptoms of hormonal imbalances. Some embodiments provide improved methods of ameliorating symptoms of menopause. Some embodiments provide improved methods of ameliorating symptoms of andropause. Some embodiments provide improved methods of ameliorating symptoms of osteoporosis. Some embodiments provide improved methods of ameliorating symptoms of improving fertility. In some embodiments, these methods comprise providing a composition comprising an effective amount of at least two of black maca root, yellow maca root, and red maca root, having a ratio. In some embodiments the ratio is from about 1:1 to about 4:1.

Some embodiments provide improved methods of ameliorating symptoms of HIV/AIDS. Some embodiments provide improved methods of ameliorating symptoms of cancer. Some embodiments provide improved methods of ameliorating discomfort related to administration of chemotherapy to treat cancer. In some embodiments, these methods comprise providing a composition comprising an effective amount of at least two of black maca root, yellow maca root, and red maca root. In some embodiments the ratio of two of the phenotypes is from about 1:1 to about 4:1.

Some embodiments provide improved methods of ameliorating symptoms of anemia. Some embodiments provide improved methods of ameliorating symptoms of chronic fatigue syndrome. Some embodiments provide improved methods of decreasing symptoms of tuberculosis. Some embodiments provide improved methods of improving mood (e.g., reducing depression). Some embodiments provide improved methods of increasing immune function. In some embodiments, these methods comprise providing a composition comprising an effective amount of at least two of black maca root, yellow maca root, and red maca root. In some embodiments the ratio of two of the phenotypes is from about 1:1 to about 4:1.

Some embodiments provide improved mitochondrial function. Some embodiments provide improved methods of improving mitochondrial function. Some embodiments provide improved methods of increasing energy. In some embodiments, these compositions and methods comprise providing a composition comprising an effective amount of at least two of black maca root, yellow maca root, and red maca root. In some embodiments the ratio of two of the phenotypes is from about 1:1 to about 4:1.

Some embodiments provide compositions comprising an amount of black maca root and an amount of red maca root, wherein the amounts have a ratio of black maca root to red maca root, and the ratio is from about 1:1 to about 4:1.

Some embodiments provide methods of increasing libido in a subject in need thereof, comprising co-administering a composition comprising a synergistically effective amount of black maca root and red maca root to the subject.

Some embodiments provide methods of decreasing cytokine activity in a subject in need thereof, comprising administering a composition comprising a synergistically effective amount of black maca root to red maca root to the subject, wherein the cytokine is selected from the group consisting of IL-1β, IL-6, IL-8, and combinations thereof.

Some embodiments provide methods of treating sexual dysfunction in humans, comprising administering a composition comprising a first amount of black maca root and a second amount of red maca root, the first and second amounts provided in a synergistic ratio.

Some embodiments provide for use of a composition for improved treatment of sexual dysfunction in humans, comprising administering a composition comprising a first amount of black maca root and a second amount of red maca root, the first and second amounts provided in a synergistic ratio.

Some embodiments provide for use of a composition for reducing muscle fatigue in a human, comprising administering a composition comprising a first amount of black maca root and a second amount of red maca root, the first and second amounts provided in a synergistic ratio. Some embodiments provide for use of a composition for reducing mental fatigue in a human, comprising administering a composition comprising a first amount of black maca root and a second amount of red maca root, the first and second amounts provided in a synergistic ratio. Some embodiments provide for use of a composition for increasing physical performance in a human, comprising administering a composition comprising a first amount of black maca root and a second amount of red maca root, the first and second amounts provided in a synergistic ratio. In some embodiments, reducing physical, mental, or muscle fatigue may be during periods of physical exertion. Some embodiments provide for use of a composition as described herein for increasing a human's stamina such as, but not limited to, physical stamina. Some embodiments provide for use of a composition as described herein for increasing a human's capacity to exert physical force, such as but not limited to during exercise. Some embodiments provide for use of a composition as described herein for increasing a human's aerobic working capacity. Some embodiments provide for use of a composition as described herein for increasing a human's anaerobic working capacity. Some embodiments provide for use of a composition as described herein for increasing the length of time for which a human can exert a physical force, such as but not limited to, during exercise.

Some embodiments provide for use of a composition as described herein for reducing the effects of physical exertion in a human comprising administering a composition as described herein. Reducing effects may include, but is not limited to, reducing lactate formation, reducing liver glycogen, reducing serum malondialdehyde, reducing muscle malondialdehyde, reducing liver malondialdehyde, reducing alanine aminotransferase, reducing aspartate aminotransferase, and/or decreasing cytokine activity. Reducing the effects of physical exertion may mean that the effects experienced by a subject such as a human are reduced or ameliorated during physical exertion or for a period afterward that would be readily ascertainable by the skilled artisan depending on the context in which this is used.

Some embodiments provide for use of a composition for reducing lactate in a human, comprising administering a composition comprising a first amount of black maca root and a second amount of red maca root, the first and second amounts provided in a synergistic ratio. In certain embodiments, the reducing of lactate in a human can be during physical exertion. In some embodiments, the lactate can be reduced by about 10 to about 50%, about 15 to about 45%, about 25 to about 50%, about 20 to about 50%, about 45%, about 50% and ranges therebetween.

Some embodiments provide for use of a composition for reducing liver glycogen in a human, comprising administering a composition comprising a first amount of black maca root and a second amount of red maca root, the first and second amounts provided in a synergistic ratio. In certain embodiments, the reducing of liver glycogen in a human can be during physical exertion. In some embodiments, the liver glycogen can be reduced by about 10 to about 40%, about 15 to about 35%, about 25 to about 35%, about 20 to about 40%, about 25%, about 35% and ranges therebetween.

Some embodiments provide for use of a composition for reducing serum malondialdeyhde (MDA) in a human, comprising administering a composition comprising a first amount of black maca root and a second amount of red maca root, the first and second amounts provided in a synergistic ratio. In certain embodiments, the reduction of serum MDA in a human can be during physical exertion. In some embodiments, the serum MDA can be reduced by about 20 to about 40%, about 25 to about 35%, about 20 to about 35%, about 25%, about 35%, and ranges therebetween.

Some embodiments provide for use of a composition for reducing muscle MDA in a human, comprising administering a composition comprising a first amount of black maca root and a second amount of red maca root, the first and second amounts provided in a synergistic ratio. In certain embodiments, the reduction of muscle MDA in a human can be during physical exertion. In some embodiments, the muscle MDA can be reduced by about 15 to about 30%, about 20 to about 25%, about 20 to about 30%, about 25%, about 20% and ranges therebetween.

Some embodiments provide for use of a composition for reducing liver MDA in a human, comprising administering a composition comprising a first amount of black maca root and a second amount of red maca root, the first and second amounts provided in a synergistic ratio. In certain embodiments, the reduction of liver MDA in a human can be during physical exertion. In some embodiments, the liver MDA can be reduced by about 20 to about 25%, about 15 to about 25%, about 20 to about 30%, about 22%, about 23%, and ranges therebetween.

Some embodiments provide for use of a composition for increasing liver superoxide dismutase (SOD) in a human, comprising administering a composition comprising a first amount of black maca root and a second amount of red maca root, the first and second amounts provided in a synergistic ratio. In certain embodiments, the increasing of liver SOD in a human can be during physical exertion. In some embodiments, the liver SOD can be increased by about 5 to about 15%, about 5 to about 10%, about 7%, about 10%, and ranges therebetween.

Some embodiments provide for use of a composition for increasing muscle SOD in a human, comprising administering a composition comprising a first amount of black maca root and a second amount of red maca root, the first and second amounts provided in a synergistic ratio. In certain embodiments, the increasing of muscle SOD in a human can be during physical exertion. In some embodiments, the muscle SOD may be increased by about 5 to about 10%, about 5 to about 15%, about 7 to about 10%, about 7%, about 6%, and ranges therebetween.

Some embodiments provide for use of a composition for increasing liver glutathione peroxidase (GSH-Px) in a human, comprising administering a composition comprising a first amount of black maca root and a second amount of red maca root, the first and second amounts provided in a synergistic ratio. In certain embodiments, the increasing of liver GSH-Px in a human can be during physical exertion. In some embodiments, the liver GSH-Px may be increased by about 2 to about 10%, about 3 to about 5%, about 3 to about 8%, about 4%, about 6%, and ranges therebetween.

Some embodiments provide for use of a composition for increasing muscle GSH-Px in a human, comprising administering a composition comprising a first amount of black maca root and a second amount of red maca root, the first and second amounts provided in a synergistic ratio. In certain embodiments, the increasing of muscle GSH-Px in a human can be during physical exertion. In some embodiments, the muscle GSH-Px is increased by about 20 to about 50%, about 25 to about 30%, about 25 to about 45%, about 35 to about 50%, about 40 to about 50%, about 25%, about 45%, about 27%, about 44%, and ranges therebetween.

Some embodiments provide for use of a composition for reducing alanine aminotransferase (ALT) in a human, comprising administering a composition comprising a first amount of black maca root and a second amount of red maca root, the first and second amounts provided in a synergistic ratio. In certain embodiments, the reduction of ALT in a human can be during physical exertion. In some embodiments, the ALT can be reduced by up to about 10%, about 5 to about 10%, about 10%, about 5%, about 4%, about 1%, and ranges therebetween.

Some embodiments provide for use of a composition for reducing aspartate aminotransferase (AST) in a human, comprising administering a composition comprising a first amount of black maca root and a second amount of red maca root, the first and second amounts provided in a synergistic ratio. In certain embodiments, the reduction of AST in a human can be during physical exertion. In some embodiments, the AST can be reduced by about 5 to about 20%, about 10 to about 20%, about 15 to about 20%, about 13%, about 15%, and ranges therebetween.

Some embodiments provide for use of a composition for reducing total cholesterol in a human, comprising administering a composition comprising a first amount of black maca root and a second amount of red maca root, the first and second amounts provided in a synergistic ratio. In certain embodiments, the reduction of total cholesterol in a human can be during physical exertion. In some embodiments, the total cholesterol may be reduced by about 10 to about 25%, about 15 to about 25%, about 20 to about 25%, about 20%, about 15%, about 22%, about 14%, and ranges therebetween.

Some embodiments provide for use of a composition for reducing triglycerides in a human, comprising administering a composition comprising a first amount of black maca root and a second amount of red maca root, the first and second amounts provided in a synergistic ratio. In certain embodiments, the reduction of triglycerides in a human can be during physical exertion.

Some embodiments provide for use of a composition for reducing nuclear factor NF-κB in a human, comprising administering a composition comprising a first amount of black maca root and a second amount of red maca root, the first and second amounts provided in a synergistic ratio. In certain embodiments, the reduction of NF-κB in a human can be during physical exertion. In some embodiments, the NF-κB can be reduced by about 15 to about 25%, about 10 to about 20%, about 20%, about 25%, and ranges therebetween.

Some embodiments provide for methods for use of a composition as described herein for regulating sirtuin pathways. Some embodiments provide for use of a composition for increasing SIRT-1 in a human, comprising administering a composition comprising a first amount of black maca root and a second amount of red maca root, the first and second amounts provided in a synergistic ratio. In certain embodiments, the increasing of SIRT-1 in a human can be during physical exertion. In some embodiments, SIRT-1 can be increased by about 25 to about 50%, up to about 50%, about 25 to about 70%, about 25%, about 35%, about 45%, about 50%, about 60%, and ranges therebetween.

Some embodiments provide for use of a composition for increasing mitochondrial transcription factor A (TFAM) in a human, comprising administering a composition comprising a first amount of black maca root and a second amount of red maca root, the first and second amounts provided in a synergistic ratio. In certain embodiments, the increasing of TFAM in a human can be during physical exertion. In some embodiments, the TFAM is increased by about 25 to about 50%, up to about 50%, about 25 to about 70%, about 25%, about 35%, about 45%, about 50%, about 60%, and ranges therebetween.

Some embodiments provide for use of a composition for increasing nuclear respiratory factor 1 (Nrf-1) in a human, comprising administering a composition comprising a first amount of black maca root and a second amount of red maca root, the first and second amounts provided in a synergistic ratio. In certain embodiments, the increasing of Nrf-1 in a human can be during physical exertion. In some embodiments, the Nrf-1 can be increased by about 50 to about 100%, about 25 to about 75%, about 50 to about 75%, about 75 to about 100%, about 50%, about 75%, about 100%, about 150%, about 100 to about 150%, about 200%, about 100 to about 200%, about 200 to about 300%, about 200%, about 300%, and ranges therebetween.

Some embodiments provide for use of a composition for increasing nuclear factor erythroid 2 (Nrf-2) in a human, comprising administering a composition comprising a first amount of black maca root and a second amount of red maca root, the first and second amounts provided in a synergistic ratio. In certain embodiments, the increasing Nrf-2 in a human can be during physical exertion. In some embodiments, the Nrf-2 can be increased by about 25 to about 50%, up to about 50%, about 25 to about 70%, about 25%, about 35%, about 45%, about 50%, about 60%, and ranges therebetween.

Some embodiments provide for use of a composition for increasing peroxisome proliferator-activated receptor-gamma coactivator (PGC-1) in a human, comprising administering a composition comprising a first amount of black maca root and a second amount of red maca root, the first and second amounts provided in a synergistic ratio. In certain embodiments, the increasing PGC-1 in a human can be during physical exertion. In some embodiments, the PGC-1 is increased by about 25 to about 50%, up to about 50%, about 25 to about 70%, about 25%, about 35%, about 45%, about 50%, about 60%, and ranges therebetween.

Some embodiments provide compositions consisting essentially of an approximately 1:4 ratio of black to red maca root.

Some embodiments provide for use of a composition for improved treatment of sexual dysfunction in humans, comprising administering a composition consisting essentially of an approximately 1:4 ratio of black to red maca root.

Some embodiments provide compositions comprising an amount of black maca root and an amount of yellow maca root, wherein the amounts have a ratio of black maca root to yellow maca root, and the ratio is about 1:1.

Some embodiments provide methods of increasing libido in a subject in need thereof, comprising co-administering a composition comprising a synergistically effective amount of black maca root and yellow maca root to the subject.

Some embodiments provide methods of decreasing cytokine activity in a subject in need thereof, comprising administering a composition comprising a synergistically effective amount of black maca root to yellow maca root to the subject, wherein the cytokine is selected from the group consisting of IL-1β, IL-6, IL-8, IP-10, IL-4, IFN-γ, and combinations thereof.

Some embodiments provide methods of treating sexual dysfunction in humans, comprising administering a composition comprising a first amount of black maca root and a second amount of yellow maca root, the first and second amounts provided in a synergistic ratio.

Some embodiments provide for use of a composition for improved treatment of sexual dysfunction in humans, comprising administering a composition comprising a first amount of black maca root and a second amount of yellow maca root, the first and second amounts provided in a synergistic ratio.

Some embodiments provide compositions consisting essentially of an approximately 1:1 ratio of black to yellow maca root.

Some embodiments provide for use of a composition for improved treatment of sexual dysfunction in humans, comprising administering a composition consisting essentially of an approximately 1:1 ratio of black to yellow maca root.

A composition consisting essentially of an approximately 1:1 ratio of black to yellow maca root for use in treating sexual dysfunction.

A more complete understanding of the compositions, methods, and uses of the compositions, will be afforded to those skilled in the art, as well as a realization of additional advantages and objects thereof, by a consideration of the following detailed description and attached appendix.

BRIEF DESCRIPTION OF THE DRAWINGS

The drawings and appendix disclose illustrative embodiments. They do not set forth all embodiments. Other embodiments may be used in addition or instead. Understanding that these Figures and appendix depict only several embodiments in accordance with the disclosure and are not to be considered limiting of its scope; the disclosure will be described with additional specificity.

DETAILED DESCRIPTION

Definitions

Figure 1:
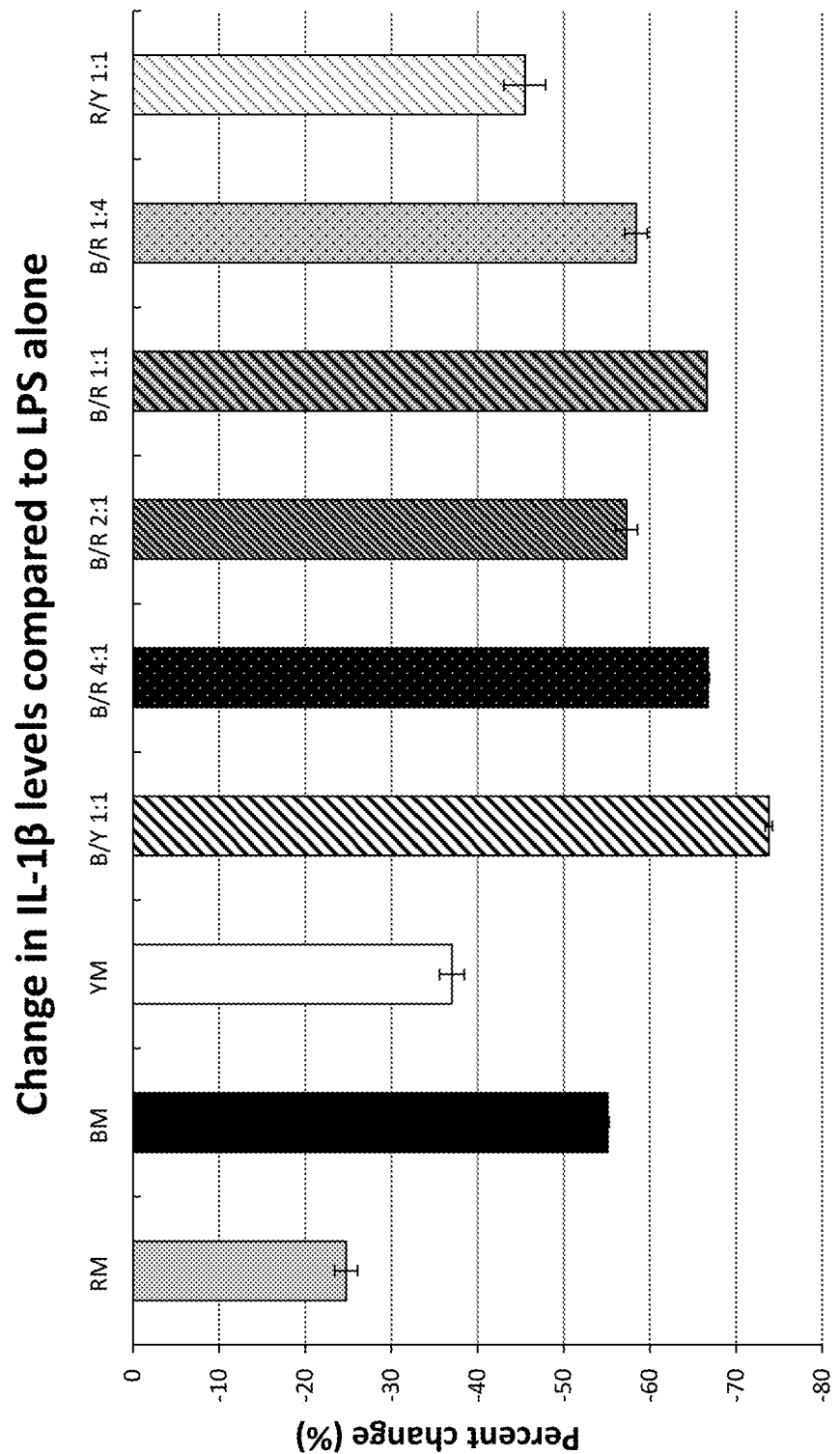
FIG. 1 represents the changes in IL-1β levels in supernatants from PBMC (peripheral blood mononuclear cell) cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the invention herein described. The meanings ascribed to various terms and phrases as used herein are illustratively explained below. It is noted that precise meaning of a particular term or phrase may differ depending on the context in which it is used.

Embodiments disclosed herein relate to the use of compositions comprising, consisting essentially of, or consisting of maca root powder. The maca root may be provided as red, yellow, or black maca, or combinations thereof, including pharmaceutically acceptable salts, hydrates, solvates, or mixtures thereof for the treatment or prevention of inflammatory disorders.

The term "treating" or "treatment" does not necessarily mean total cure. Any alleviation of any undesired signs or symptoms of the disease to any extent or the slowing down of the progress, or even prevention of the disease or condition can be considered treatment. As used herein, the term "providing" (a substance) refers to supplying, making available, or administering the substance. As used herein, the term "subject" encompasses animals, preferably mammals, and most preferably humans. The term "subject" may be used interchangeably with "patient."

Some embodiments provide compositions and methods of treating subjects with compositions that comprise, consist essentially of, or consist of an effective amount of maca. Some embodiments provide compositions and method of treating subjects with compositions that comprise, consist essentially of, or consist of an effective amount of maca and an effective amount of a second agent.

A "maca composition," as used herein, generally refers to a composition comprising at least two different maca root phenotypes (although it can refer to a single maca root phenotype in certain embodiments), where the different phenotypes are denoted by different colors resulting from particular compositional characteristics. Examples of maca compositions with different phenotypes include but are not limited to yellow and black, black and red, and red and yellow. In some aspects, the maca compositions may include different maca root phenotypes provided in different molar, weight, or volume ratios. Maca compositions may include red, black, purple, green, yellow, blue maca root phenotypes and combinations thereof in ratios that would be envisaged by the skilled artisan in light of the disclosure contained herein.

The term "sexual dysfunction," as used herein, refers to difficulty experienced by a subject during any stage of a normal sexual activity, including but not limited to physical pleasure, desire, preference, arousal or orgasm. Sexual dysfunction also includes desire disorders—lack of sexual desire or interest in sex; arousal disorders—inability to become physically aroused or excited during sexual activity; orgasm disorders—delay or absence of orgasm (climax); and pain disorders—pain during intercourse.

Identifying an individual with a sexual dysfunction or in need of treatment for sexual dysfunction or symptoms thereof, may include, for example, identifying one or more of the following disorders in accordance with the fourth edition of the Diagnostic and Statistical Manual of Mental Disorders: hypoactive sexual desire disorder, sexual aversion disorder, female sexual arousal disorder, male erectile disorder, female orgasmic disorder, male orgasmic disorder, anorgasmia, dyspareunia, and/or vaginismus. Identifying an individual with a sexual dysfunction or in need of treatment for sexual dysfunction or symptoms thereof may be made by, or with the assistance of, a medical professional. In some aspects, identifying an individual with a sexual dysfunction or in need of treatment for sexual dysfunction or symptoms thereof, includes self-identification by the patient.

The term "libido," as used herein, refers to a subject's overall sexual drive or desire for sexual activity. A subject in need of increased libido may include a person diagnosed or self-diagnosed with one or more sexual dysfunctions or disorders.

The term "mitochondrial function", as used herein, refers to the a subject's mitochondria's ability to synthesize adenosine triphosphate (ATP), measured and determined by methods known those of skill in the art.

An "effective amount," as used herein includes within its meaning a non-toxic but sufficient amount of a compound active ingredient or composition comprising the same for use in the embodiments disclosed herein to provide the desired therapeutic effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, an embodiment may not specify an exact "effective amount". For any given case; an appropriate "effective amount" may be envisaged by the skilled artisan in light of the context of the term and the disclosure contained herein.

The term "physical exertion" as used herein may refer to exercise, such as but not limited to, anaerobic exercise, aerobic exercise, weight-lifting, cross-training, athletic competition, tasks involving muscular exertion (e.g., manual labor), and the like, along with combinations of these. As used herein, "physical exertion" may refer to these activities as are engaged in by a mammal, such as a human. "Physical exertion" can also refer to undesirable effects experienced by a mammal, such as a human, shortly after the activities described in this paragraph. The meaning and scope of this term would be immediately envisaged by the skilled artisan when considering the scope in which it is used.

In some aspects, "effective amount" of total maca root, provided as one, two or more phenotypes of maca, disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of a maca root composition. Accordingly, in some embodiments, the effective amount of total maca root in a compositions disclosed herein can be about 1 mg to about 5 g, preferably per day. For example, the amount of total maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values. In some aspects, the "effective amount" of total maca root is about 3 grams of maca root per day per individual, provided as two or more phenotypes of maca, to the individual regardless of individual's body weight.

By way of example, an "effective amount" of black maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of black maca root. Accordingly, in some embodiments, the effective amount of black maca root in compositions disclosed herein can be about 1 mg to about 5 g, preferably per day. For example, the amount of black maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, an "effective amount" of red maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of red maca root. Accordingly, in some embodiments, the effective amount of red maca root in compositions disclosed herein can be about 1 mg to about 5 g, preferably per day. For example, the amount of red maca root can be about 1 mg to about 5 g, preferably per day. For example, the amount of red maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, an "effective amount" of yellow maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of yellow maca root. Accordingly, in some embodiments, the effective amount of yellow maca root in compositions disclosed herein can be about 1 mg to about 5 g, preferably per day. For example, the amount of yellow maca root can be about 1 mg to about 5 g, preferably per day. For example, the amount of yellow maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, an "effective amount" of blue maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of blue maca root. Accordingly, in some embodiments, the effective amount of blue maca root in compositions disclosed herein can be about 1 mg to about 5 g, preferably per day. For example, the amount of blue maca root can be about 1 mg to about 5 g, preferably per day. For example, the amount of blue maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, an "effective amount" of purple maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of purple maca root. Accordingly, in some embodiments, the effective amount of purple maca root in compositions disclosed herein can be about 1 mg to about 5 g, preferably per day. For example, the amount of purple maca root can be about 1 mg to about 5 g, preferably per day. For example, the amount of purple maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, an "effective amount" of green maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of green maca root. Accordingly, in some embodiments, the effective amount of green maca root in compositions disclosed herein can be about 1 mg to about 5 g, preferably per day. For example, the amount of green maca root can be about 1 mg to about 5 g, preferably per day. For example, the amount of green maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

Examples of the therapeutically effective amounts listed above, can, in some embodiments be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

As used herein, a "second agent" refers to an additional active compound or compounds (i.e., not excipients, diluents, or vehicles). Exemplary second agents include vitamins, minerals, hormones, non-steroidal anti-inflammatories, and anti-depressants.

In some embodiments, the maca composition is provided in combination with a second agent, e.g., within a single dosage form, such as a single oral dosage form or an oral suspension dosage form. In some embodiments, the maca composition is provided with a second agent in a multi-unit dosage form. In some embodiments, the maca composition is provided suspended in a solution of the second agent. Accordingly, provided herein are compositions that comprise, consist essentially of, or consist of maca and a second agent.

The terms "macamide" and "macamene," as used herein refer to specific classes of compounds found in maca roots.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

Some embodiments provide maca compositions comprising at least two maca root phenotypes. Some embodiments provide maca compositions comprising at least three maca root phenotypes. Some embodiments provide maca compositions comprising at least four maca root phenotypes. Some embodiments provide maca compositions comprising at least five maca root phenotypes. Some embodiments provide maca compositions comprising two, three, four, or five maca root phenotypes.

In some embodiments, a composition comprises an effective amount of black maca and an effective amount of yellow maca. In some embodiments, a composition comprises an effective amount of black maca and an effective amount of red maca. In some embodiments, a composition comprises an effective amount of black maca and an effective amount of purple maca. In some embodiments, a composition comprises an effective amount of black maca and an effective amount of green maca. In some embodiments, a composition comprises an effective amount of black maca and an effective amount of blue maca.

In some embodiments, a composition comprises an effective amount of red maca and an effective amount of yellow maca. In some embodiments, a composition comprises an effective amount of red maca and an effective amount of green maca. In some embodiments, a composition comprises an effective amount of red maca and an effective amount of purple maca. In some embodiments, a composition comprises an effective amount of red maca and an effective amount of blue maca.

In some embodiments, a composition comprises an effective amount of red maca, an effective amount of yellow maca, and an effective amount of black maca.

In some embodiments, the maca root phenotypes are present in a ratio of 1:1, 1:2, 1:3, 1:4, 1:5, 1:6, 1:7, 1:8, 1:9, 1:10, 1:15, 1:20, 1:30, 1:40, 1:50, 1:1:1, 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:109:9, 1:10:10, or any ratio in between.

In some embodiments, the maca compositions comprise 1:1 black-red maca root. In some embodiments, the maca compositions comprise 2:1 black-red maca root. In some embodiments, the maca compositions comprise 4:1 black-red maca root. In some embodiments, the maca compositions comprise 1:4 black-red maca root. In some embodiments, the maca compositions comprise 1:1 black-yellow maca root. In some embodiments, the maca compositions comprise 1:1 yellow-red maca root.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

In some embodiments, the compositions provided herein are formulated for intradermal, intramuscular, intraperitoneal, intravenous, subcutaneous, intranasal, epidural, oral, sublingual, intranasal, intracerebral, intravaginal, transdermal, rectal, ophthalmic, or topical delivery. The preferred mode of administration is left to the discretion of the practitioner, and will depend in part upon the site of the medical condition. In most instances, administration will result in the release of the compounds of the embodiments disclosed herein into the bloodstream.

In some embodiments, the compositions provided herein comprise, consist essentially of, or consist of a combination of an effective amount of maca, which can be any one of, or combinations of, the phenotypes described herein. In embodiments, compositions provided herein comprise, consist essentially of, or consist of a combination of a synergistically effective amount of maca, which can be any one of, or combinations of, the phenotypes described herein.

In some embodiments, maca is provided with a nutritionally acceptable carrier or a pharmaceutically acceptable carrier. As used herein, the phrase "nutritionally acceptable carrier", "nutritionally acceptable excipient", "pharmaceutically acceptable carrier", or "pharmaceutically acceptable excipient" refers to nutritionally or pharmaceutically acceptable materials, compositions or vehicles, suitable for administering compounds of the embodiments disclosed herein to mammals. The carriers can include liquid or solid filler, diluent, excipient, solvent or encapsulating material, involved in carrying or transporting the subject agent from one organ, or portion of the body, to another organ, or portion of the body. Carriers can be "acceptable" in the sense of being compatible with the other ingredients of the formulation and not injurious to the patient. Some examples of materials which can serve as nutritionally or pharmaceutically acceptable carriers include, but are not limited to: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In some embodiments, the nutritionally or pharmaceutically acceptable carrier can be suitable for intravenous administration. In some embodiments, the nutritionally or pharmaceutically acceptable carrier can be suitable for locoregional injection.

The term "composition" refers to pharmaceutically and nutraceutically acceptable preparation, and includes preparations suitable for administration to subjects, e.g., humans. When the compounds of the embodiments disclosed herein are administered to subjects, e.g., humans, they can be given by itself or as a composition containing, for example, 0.1 to 99.5% (more preferably, 0.5 to 90%) of active ingredients in combination with a nutritionally or pharmaceutically acceptable carrier. The amount of active agents incorporated into the multiple unit dosage form of the embodiments disclosed herein is quantum sufficiat to achieve the desired effect.

For oral administration, the compositions disclosed herein can be provided as a tablet, aqueous or oil suspension, dispersible powder or granule, emulsion, hard or soft capsule, syrup, elixir, chew, or beverage. Solid dosage forms such as tablets and capsules may be comprise an enteric coating. Compositions intended for oral use can be prepared according to any method known in the art for the manufacture of compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the described herein admixed with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

A chewable dosage form can be made with candy bases such as rice syrup, maltitol syrup, sugar/corn syrup, etc. The base can either contain sugar or be sugarless. Additives such as palm oil, sunflower oil, soy lecithin, and glycerin can be included to formulate the chewable dose. The chewable can be flavored using natural and/or artificial flavors.

Oil suspensions can be formulated by suspending the active ingredient in a vegetable oil, such as *arachis* oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

It will be appreciated that the amount of the compound may be combined with a carrier material to produce a single dosage form. Such forms will vary depending upon the host treated and the particular mode of administration.

When administered to a subject, e.g., to an animal for veterinary use or for improvement of livestock, or to a human for therapeutic use, the compositions disclosed herein are administered in isolated form or as the isolated form in a therapeutic composition. As used herein, "isolated" means that the compositions disclosed herein are separated from other components of either (a) a natural source, such as a plant or cell or food, preferably bacterial culture, or (b) a synthetic organic chemical reaction mixture. Preferably, via conventional techniques, the compositions disclosed herein are purified. As used herein, "purified" means that when isolated, the isolate contains at least 95%, preferably at least 98% of the composition.

Aqueous suspensions may contain the compound disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the maca. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein maca powder is dissolved in an aqueous constituent to gradually release over time, can be prepared by copolymerization of hydrophilic mono-olefinic monomers such as ethylene glycol methacrylate. Matrix devices, wherein maca powder is dispersed in a matrix of carrier material, can be used. The carrier can be porous, non-porous, solid, semi-solid, permeable or impermeable. Alternatively, a device comprising a central reservoir of maca powder surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Embodiments of the compositions described herein may be administered once, twice, or three times per day. In some aspects, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. Active agents that can make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

Active ingredients (e.g., maca root and other pharmaceutical or supplemental ingredients that may be present) can be administered by the oral route in solid dosage forms, such as tablets, capsules, and powders, or in liquid dosage forms, such as elixirs, syrups, and suspensions. Each active ingredient can be administered by the parenteral route in liquid dosage forms. The pharmaceutical composition is preferably made in the form of a dosage unit containing a particular amount of each active ingredient.

In general, the pharmaceutical dosage forms of compositions of this application can be prepared by conventional techniques, as are described in *Remington's Pharmaceutical Sciences*, a standard reference in this field [Gennaro A R, Ed. *Remington: The Science and Practice of Pharmacy*. $20^{th}$ Edition. Baltimore: Lippincott, Williams & Williams, 2000]. For therapeutic purposes, the active components of this combination therapy application are ordinarily combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art.

The compositions disclosed herein can preferably be formulated with other active ingredients such as a slow-acting agent or long acting agent in addition to drugs or alone before meals and/or after meals. Effective doses may be extrapolated from dose-response curves derived from in vitro or animal model test systems. Such animal models and systems are well known in the art.

Synergistic Compositions of Maca Root

In some embodiments, the compositions provided herein comprise a synergistically effective amount of maca phenotypes selected together to provide a greater than additive effect. This greater than additive effect can include, but is not limited to, an increased libido and/or decreased systemic inflammation. A "synergistically effective amount" as used herein refers to the amount of one component of a composition necessary to elicit a synergistic effect with another component present in the composition. A "synergistic effect" as used herein refers to a result that is unexpectedly superior than what would be expected when either component is administered alone. The exact synergistically effective amounts of the active ingredients disclosed herein required will vary from subject to subject depending on factors such as the species being treated, the age and general condition of the subject, co-morbidities, the severity of the condition being treated, the particular agents being administered, the weight of the subject, and the mode of administration, and so forth. Thus, embodiments may not specify an exact "synergistic amount." However, for any given case, an appropriate "synergistically effective amount" may be envisaged by the skilled artisan in light of the context of the term and the disclosure contained herein.

By way of example, a "synergistically effective amount" of the black maca root disclosed herein can be, for example 01 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of black maca root. Accordingly, in some embodiments, the synergistically effective amount of black maca root in compositions disclosed herein can be about 1 mg to about 5 g, preferably per day. For example, the amount of black maca root can be about 1 mg to about 5 g, preferably per day. For example, the amount of black maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, a "synergistically effective amount" of the red maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of red maca root. Accordingly, in some embodiments, the synergistically effective amount of red maca root in compositions disclosed herein can be about 1 mg to about 3 g, preferably per day. For example, the amount of red maca root can be about 1 mg to about 5 g, preferably per day. For example, the amount of red maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, a "synergistically effective amount" of the yellow maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of yellow maca root. Accordingly, in some embodiments, the synergistically effective amount of yellow maca root in compositions disclosed herein can be about 1 mg to about 5 g, preferably per day. For example, the amount of yellow maca root can be about 1 mg to about 5 g, preferably per day. For example, the amount of yellow maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, a "synergistically effective amount" of the green maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of green maca root. Accordingly, in some embodiments, the synergistically effective amount of green maca root in compositions disclosed herein can be about 1 mg to about 5 g, preferably per day. For example, the amount of green maca root can be about 1 mg to about 5 g, preferably per day. For example, the amount of green maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, a "synergistically effective amount" of the blue maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of blue maca root. Accordingly, in some embodiments, the synergistically effective amount of blue maca root in compositions disclosed herein can be about 1 mg to about 5 g, preferably per day. For example, the amount of blue maca root can be about 1 mg to about 5 g, preferably per day. For example, the amount of blue maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

By way of example, a "synergistically effective amount" of the purple maca root disclosed herein can be, for example 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 185 mg/kg, 190 mg/kg, 195 mg/kg, 200 mg/kg, or more, or any fraction in between of purple maca root. Accordingly, in some embodiments, the synergistically effective amount of purple maca root in compositions disclosed herein can be about 1 mg to about 5 g, preferably per day. For example, the amount of purple maca root can be about 1 mg to about 5 g, preferably per day. For example, the amount of purple maca root can be 1 mg, 10 mg, 100 mg, 500 mg, 1 g, 1.5 g, 2 g, 2.5 g, 3 g, 3.5 g, 4 g, 4.5 g, or 5 g, or more, or any range or amount in between any two of the preceding values.

In some embodiments, the composition comprises a synergistically effective amount of black maca and a synergistically effective amount of yellow maca. In some embodiments, the composition comprises a synergistically effective amount of black maca and a synergistically effective amount of red maca. In some embodiments, the composition comprises a synergistically effective amount of black maca and a synergistically effective amount of yellow maca. In some embodiments, the composition comprises a synergistically effective amount of red maca and a synergistically effective amount of yellow maca.

In some embodiments, the composition comprises a synergistically effective amount of red maca, a synergistically effective amount of yellow maca, and a synergistically effective amount of black maca. Certain embodiments may comprise a synergistically effective amount of yellow, red, black, green, blue, or purple mace and combinations thereof.

In some embodiments, the maca root phenotypes present in a synergistically effective amount are present in a ratio of 1:1, 1:2, 1:3, 1:4, 1:5, 1:6, 1:7, 1:8, 1:9, 1:10, 1:15, 1:20, 1:30, 1:40, 1:50, 1:1:1, 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:109:9, 1:10:10, or any ratio in between.

In some embodiments, the synergistic maca compositions comprise 1:1 black-yellow maca root. In some embodiments, the synergistic maca compositions comprise 1:1 yellow-red maca root. In some embodiments, the synergistic maca compositions comprise 1:1 black-red maca root. In some embodiments, the synergistic maca compositions comprise 2:1 black-red maca root. In some embodiments, the synergistic maca compositions comprise 4:1 black-red maca root. In some embodiments, the synergistic maca compositions comprise 1:4 black-red maca root.

Examples of embodiments of compositions of synergistic combinations of maca are compared to the composition of prior art maca as shown in Table 1 as follows:

TABLE 1

| | JDS Blend A Maca Y:B 1:1 | JDS Blend B Maca Y:B 1:1 | Natural Maca |
|---|---|---|---|
| Total Sugar (g/100 g) | 30.6 | 34.9 | 12.3 |
| Protein (g/100 g) | 15 | 11.8 | 9.77 |
| Total Amino Acids (mg/100 g) | 11598 | 9825 | 8869 |
| pH | 5.15 | 5.26 | 5.41 |
| Free Fatty Acids as Oleic (g/100 g) | 0.36 | 0.34 | 0.86 |
| Total Polyphenols (Gallic Acid Equivalents) (mg/100 g) | 367 | 407 | 204 |
| Glucosinolates by HPLC* (umol/g) | | | |
| Glucoalyssin | 0.345 | 0.212 | <0.2 |
| 4-hydroxyglucobrassicin | 0.486 | 0.254 | <0.2 |
| Gluctoropaeolin | 12.9 | 7.77 | 3.98 |
| Total Glucosinolates mg/100 g | 567 | 339 | 163 |
| Total Glucosinolates umol/g | 13.8 | 8.23 | 3.98 |

Compositions of a black and yellow maca synergistic combination are comprised of certain components including, but not limited to, those shown in Table 1. Embodiments of the invention as disclosed herein comprise particular isolated phenotypes of maca that are then combined in particular ratios as set forth herein to achieve their unique and unexpectedly superior results than that which exists in the prior art. Without being bound by theory, the inventors have also determined particular ranges of components of certain maca compositions, which are produced by the combination of certain isolated phenotypes, which are different than that which exists in the prior art. These differences are evidenced by the uniquely developed compositions and by their uniquely configured chemical compositions as described herein. In some embodiments, processing of the maca compositions can further be employed to achieve compositions including those shown in Table 1. In some embodiments, further processing may be employed (which may include heating, or further extractions in water or alcohol) to alter (i.e., increase or decrease) the particular components of the maca compositions such as those listed in Table 1. In certain embodiments a maca composition comprises between about 15 and about 40 grams of total sugar per 100 grams of maca composition. In certain embodiments, a maca composition can comprise about 15, about 20, about 25, about 30, about 35, about 40, between about 25 and about 35, or between about 30 and about 35 grams of total sugar per 100 grams of maca composition and ranges therebetween. Some embodiments of a maca composition may comprise greater than about 15 grams of total sugar per 100 g of maca composition.

In certain embodiments, a maca composition comprises between about 10 and about 15 grams of protein per 100 grams of maca composition. In certain embodiments, a maca composition can comprise about 10, about 12, about 15, between about 10 and about 12, between about 12 and about 15, or between about 11 and about 15 grams of protein per 100 grams of maca composition and ranges therebetween. Some embodiments of a maca composition may comprise greater than about 10 grams of protein per 100 grams of maca composition.

In certain embodiments, a maca composition comprises between about 9000 and about 12000 mg of total amino acids per 100 grams of maca composition. In certain embodiments, a maca composition comprises about 9000, about 9750, about 9800, about 10000, about 11000, about 11500, or about 12000 mg of total amino acids per 100 grams of maca composition, and ranges therebetween. In certain embodiments, a maca composition between about 9800 and about 11750, between about 9500 and about 11500, between about 9000 and about 10000, or between about 10000 and about 11600 mg of total amino acids per 100 grams of maca composition and ranges therebetween. Certain embodiments of a maca composition may comprise greater than about 9000 mg of total amino acids per 100 grams of maca composition. Certain embodiments may comprise between about 3000 mg and about 5000 mg of proline per 100 grams of maca composition. Certain embodiments may comprise between about 2500 mg and about 6000 mg, between about 3500 mg and about 4500 mg of proline per 100 grams of maca composition and ranges therebetween.

In certain embodiments, a maca composition has a pH of less than about 5.4. In certain embodiments, a maca composition can have a pH of between about 5.1 and about 5.3, between about 5.15 and about 5.26, between about 5.1 and about 5.4 and ranges therebetween.

In certain embodiments, a maca composition can comprise between about 0.3 and about 0.8 grams of free fatty acids as oleic acid per 100 grams of maca composition. In certain embodiments, a maca composition can comprise between about 0.3 and about 0.4, between about 0.34 and about 0.36, between about 0.35 and about 0.8, or about 0.5 and about 0.8 grams of free fatty acids as oleic acid per 100 grams of maca composition and ranges therebetween. In certain embodiments, a maca composition can comprise about 0.35, about 0.3, about 0.4, about 0.5, or about 0.8 grams of free fatty acids as oleic acid per 100 grams of maca composition and ranges therebetween. Some embodiments of a maca composition may comprise less than about 0.8 grams of free fatty acids as oleic acid per 100 grams of maca composition.

Certain embodiments of a maca composition can comprise a predetermined amount of total polyphenols. In some embodiments, total polyphenols can comprise gallic acid equivalents. In certain embodiments, a maca composition can comprise between about 250 and about 450, between about 250 and about 300, between about 250 and about 350, between about 350 and about 400, between about 250 and about 375, or between about 350 and about 415 mg of total polyphenols per 100 grams of maca composition and ranges therebetween. In certain embodiments, a maca composition can comprise about 250, about 350, about 365, about 375, about 400, or about 415 mg of total polyphenols per 100 grams of maca composition and ranges therebetween. In some embodiments, a maca composition can comprise greater than about 250 mg of total polyphenols per 100 grams of maca composition.

In certain embodiments, a maca composition can comprise between about 0.2 and about 0.35 umol of glucoalyssin per gram of maca composition. In certain embodiments, a maca composition can comprise between about 0.2 and about 0.3, between about 0.25 and about 0.35, or between about 0.30 and about 0.35 umol of glucoalyssin per gram of maca composition and ranges therebetween. In certain embodiments, a maca composition may comprise about 0.2, about 0.3, or about 0.35 umol of glucoalyssin per gram of maca composition. In some embodiments, a maca composition can comprise greater than about 0.2 umol of glucoalyssin per gram of maca composition.

In certain embodiments, a maca composition can comprise between about 0.2 and about 0.5 umol of 4-hydroxyglucobrassicin per gram of maca composition. In certain embodiments, a maca composition can comprise between about 0.2 and about 0.3, between about 0.25 and about 0.5, between about 0.4 and about 0.5, between about 0.4 and about 0.49 or between about 0.30 and about 0.4 umol of 4-hydroxyglucobrassicin per gram of maca composition and ranges therebetween. In certain embodiments, a maca composition may comprise about 0.2, about 0.25, about 0.35 or about 0.49 umol of 4-hydroxyglucobrassicin per gram of maca composition and ranges therebetween. In some embodiments, a maca composition can comprise greater than about 0.2 umol of 4-hydroxyglucobrassicin per gram of maca composition.

In certain embodiments, a maca composition can comprise between about 5 and about 13 umol of gluctoropaeolin per gram of maca composition. In certain embodiments, a maca composition can comprise between about 7 and about 13, between about 8 and about 13, between about 5 and about 8, between about 10 and about 13, or between about 12 and about 13 umol of gluctoropaeolin per gram of maca composition and ranges therebetween. In certain embodiments, a maca composition can comprise about 5, about 8, about 10, about 12, or about 13 umol of gluctoropaeolin per gram of maca composition and ranges therebetween. In some embodiments, a maca composition can comprise greater than about 5 umol of gluctoropaeolin per gram of maca composition.

In certain embodiments, a maca composition may comprise a predetermined amount of glucosinolates. In some embodiments, the glucosinolates may be selected from the group consisting of glucoalyssin, 4-hydroxyglucobrassicin, and gluctoropaeolin. In certain embodiments, a maca composition can comprise between about 200 and about 700 mg of total glucosinolates per 100 grams of maca composition. In certain embodiments, a maca composition can comprise between about 200 and about 350, between about 330 and about 570, between about 500 and about 575, between about 500 and about 700, between about 600 and about 700, or between about 300 and about 350 mg of total glucosinolates per 100 g of maca composition and ranges therebetween. In some embodiments, a maca composition can comprise about 200, about 340, about 350, about 500, about 570, about 575, about 600, about 650, or about 700 mg of total glucosinolates per 100 g of maca composition and ranges therebetween. In certain embodiments, a maca composition can comprise greater than about 200 mg of total glucosinolates per 100 grams of maca composition.

In certain embodiments, a maca composition can comprise between about 5 and about 14 umol of total glucosinolates per gram of maca composition. In certain embodiments, a maca composition can comprise between about 5 and about 8, between about 8 and about 14, between about 8 and about 8.25, between about 13 and about 14, or between about 8.5 and about 13.5 umol of total glucosinolates per gram of maca composition and ranges therebetween. In some embodiments, a maca composition can comprise about 5, about 8, about 8.5, about 8.25, about 13, or about 14, umol of total glucosinolates per gram of maca composition and ranges therebetween. In some embodiments, a maca composition can comprise greater than about 5 umol of total glucosinolates per gram of maca composition.

The following Examples are provided for illustrative purposes and are not in any way intended to limit the scope of the application or claims.

EXAMPLES

Aqueous and ethanolic extracts of processed maca roots and maca root blends were obtained using standard extraction methods. The aqueous extracts, as shown in Table 2, were used in the following examples. Additional data can be found in Appendix A, which was attached to U.S. Application No. 62/411,977 and incorporated in its entirety, including the drawings.

TABLE 2

Maca Root Preparations

| Maca root | Color/Blend | Product handling |
| --- | --- | --- |
| 1. Maca root | Black | Aqueous |
| 2. Maca root | Red | Aqueous |
| 3. Maca root | Yellow | Aqueous |
| 4. Maca blend | Black/Red 2:1 blend | Aqueous |
| 5. Maca blend | Black/Red 4:1 blend | Aqueous |
| 6. Maca blend | Black/Red 1:1 blend | Aqueous |
| 7. Maca blend | Black/Red 1:4 blend | Aqueous |
| 8. Maca blend | Black/Yellow 1:1 blend | Aqueous |
| 9. Maca blend | Red/Yellow 1:1 | Aqueous |

Example 1: Effects of Maca Compositions Under Inflammatory Conditions

Human peripheral blood mononuclear cell (PBMC) cultures were treated with the highly inflammatory bacterial lipopolysaccharide (LPS) from *E. coli* (positive control). The cultures were incubated for 24 hours, after which the cells and the culture supernatants were harvested and used to monitor the reactions in each culture. The supernatant from each culture was used for testing of a panel of pro- and anti-inflammatory cytokines and anti-viral chemokines, using a Luminex magnetic bead array and the MagPix® multiplexing system to test for selected cytokines, as shown in FIGS. 1-11.

The testing for cellular activation was performed such that all treatments, including each dose of test product and each positive and negative control, were tested in triplicate. The testing of cytokine production was tested in duplicate. The tests were performed on cells from one healthy blood donor.

Average and standard deviation for each data set, as well as statistical comparison, were calculated using Microsoft Excel. Statistical analysis of the in vitro data was performed by comparison of the measures (duplicates for Luminex cytokine testing) for a specific test condition to relevant controls. Tail: a two-tailed t-test was applied, because a test material may either induce or inhibit a specific assay outcome. Type: an independent, or 'unpaired', test was applied, because each cell culture is unique, positioned in different areas of a microplate with slightly different environmental exposures, and handling through the assay (such as pipetting), although uniform, was not identical. Statistical significance was indicated if $p<0.05$ and a high level of significance was indicated if $p<0.01$.

The effects of maca roots and blends on PBMC cytokine production were tested following the protocol described above. Below is a table listing the ten cytokines/chemokines, and a brief description of their major mode of action. Following this description are the results of the testing on PBMC culture supernatants and after administering doses of 0.5 mg/mL test product.

FIG. 1 represents the changes in IL-1β levels in supernatants from PBMC (peripheral blood mononuclear cell) cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 2:
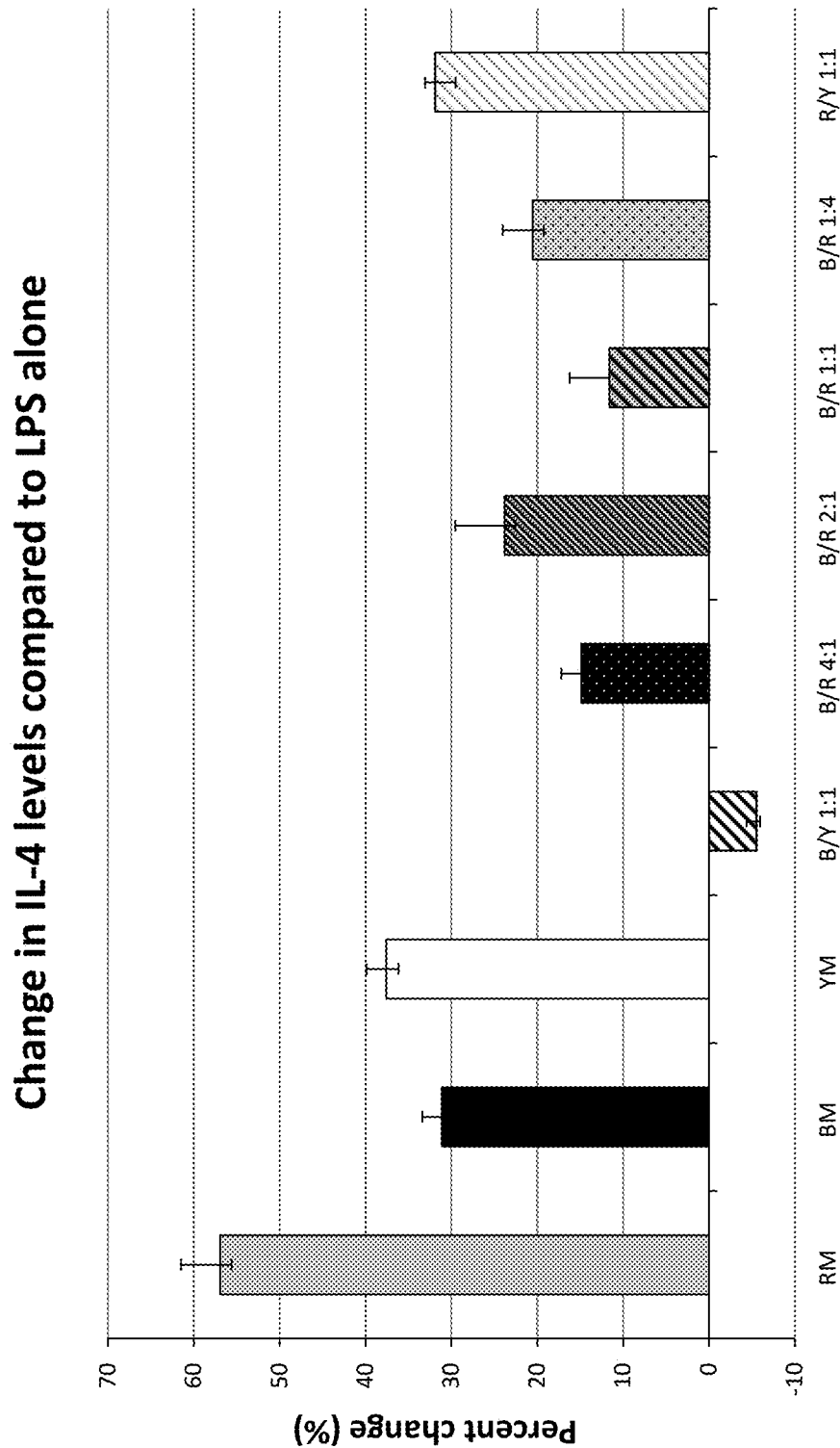
FIG. 2 represents the change in IL-4 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 2 represents the change in IL-4 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 3:
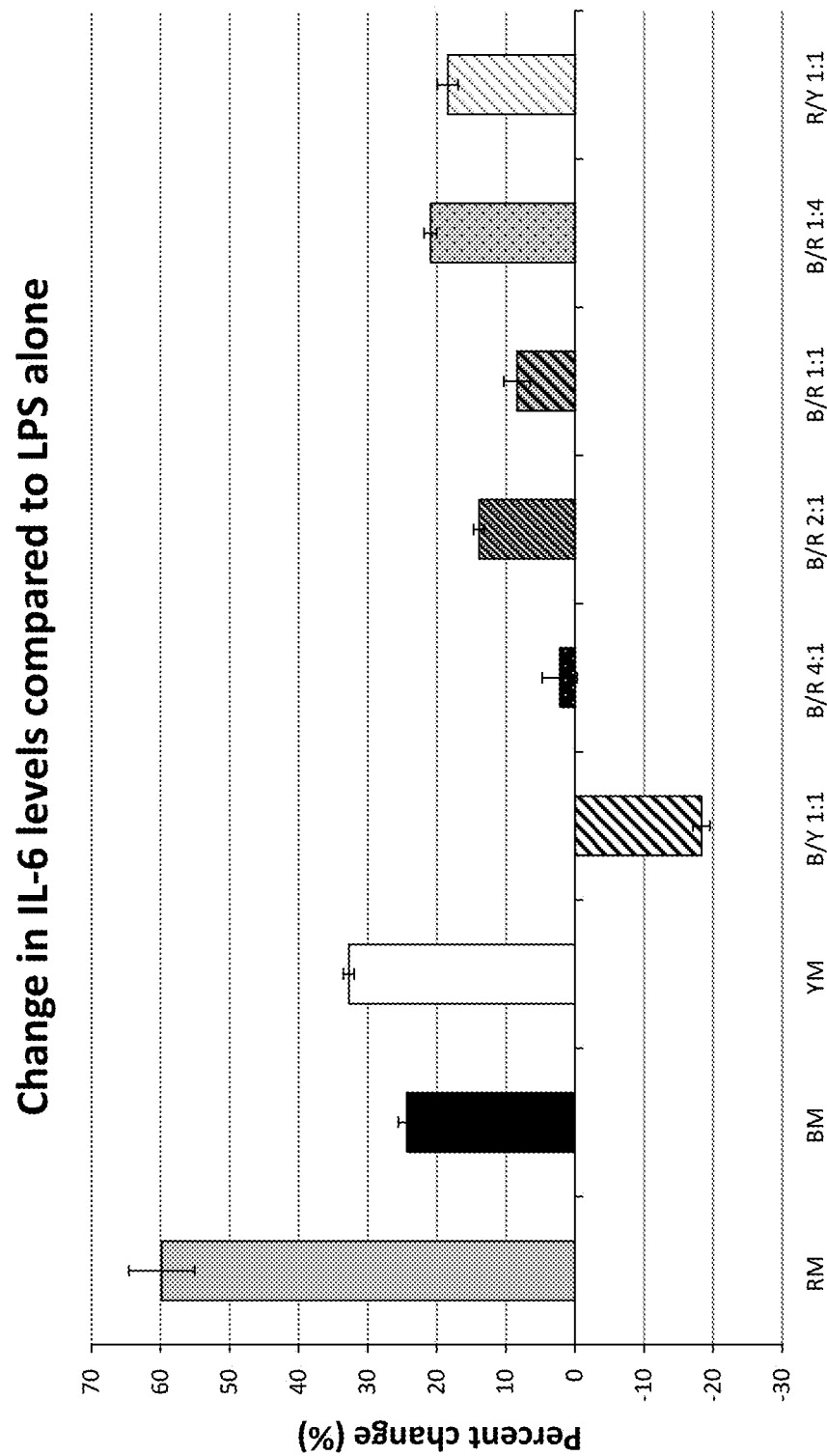
FIG. 3 represents the change in IL-6 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 3 represents the change in IL-6 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 4:
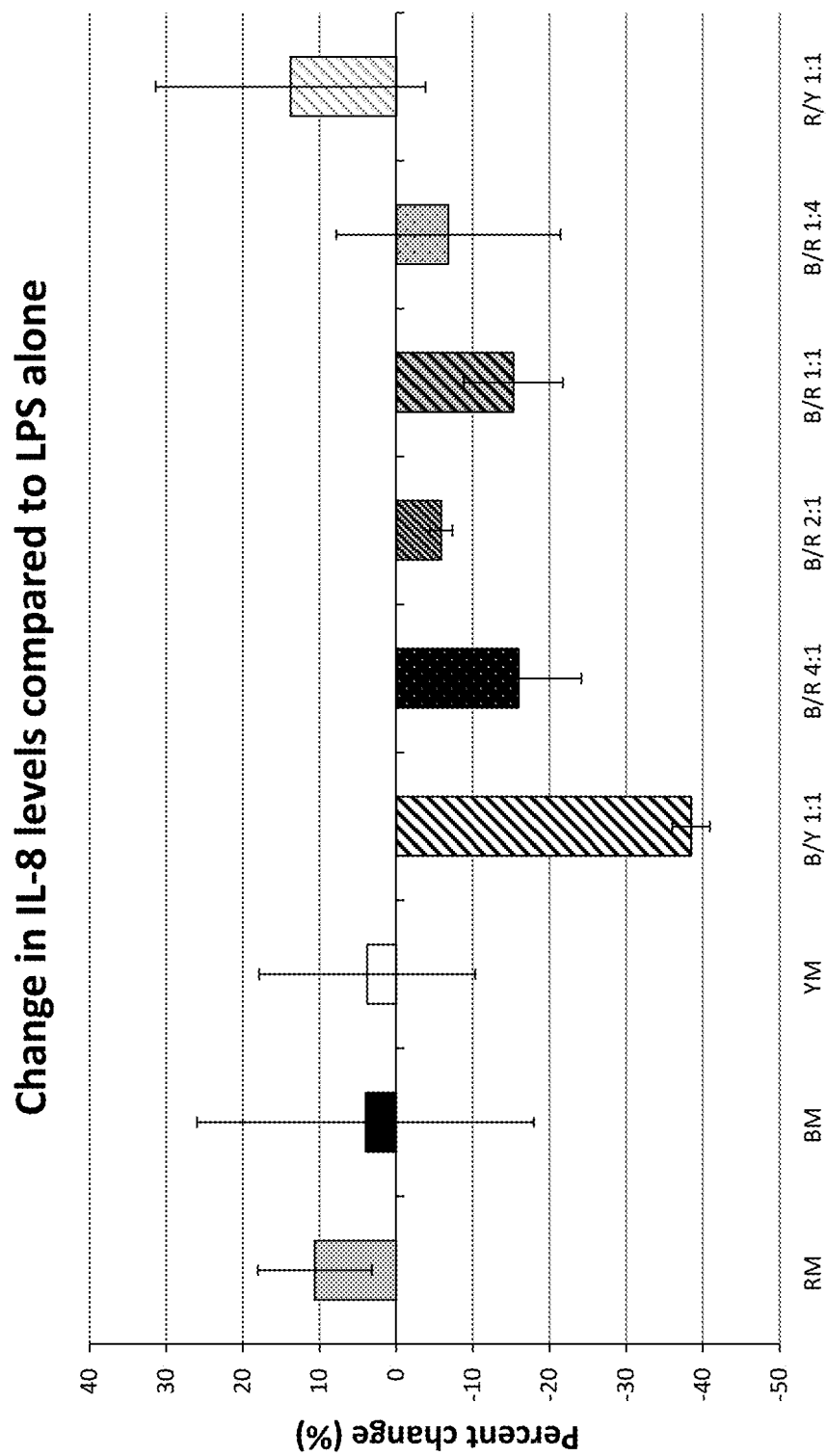
FIG. 4 represents the change in IL-8 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 4 represents the change in IL-8 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 5:
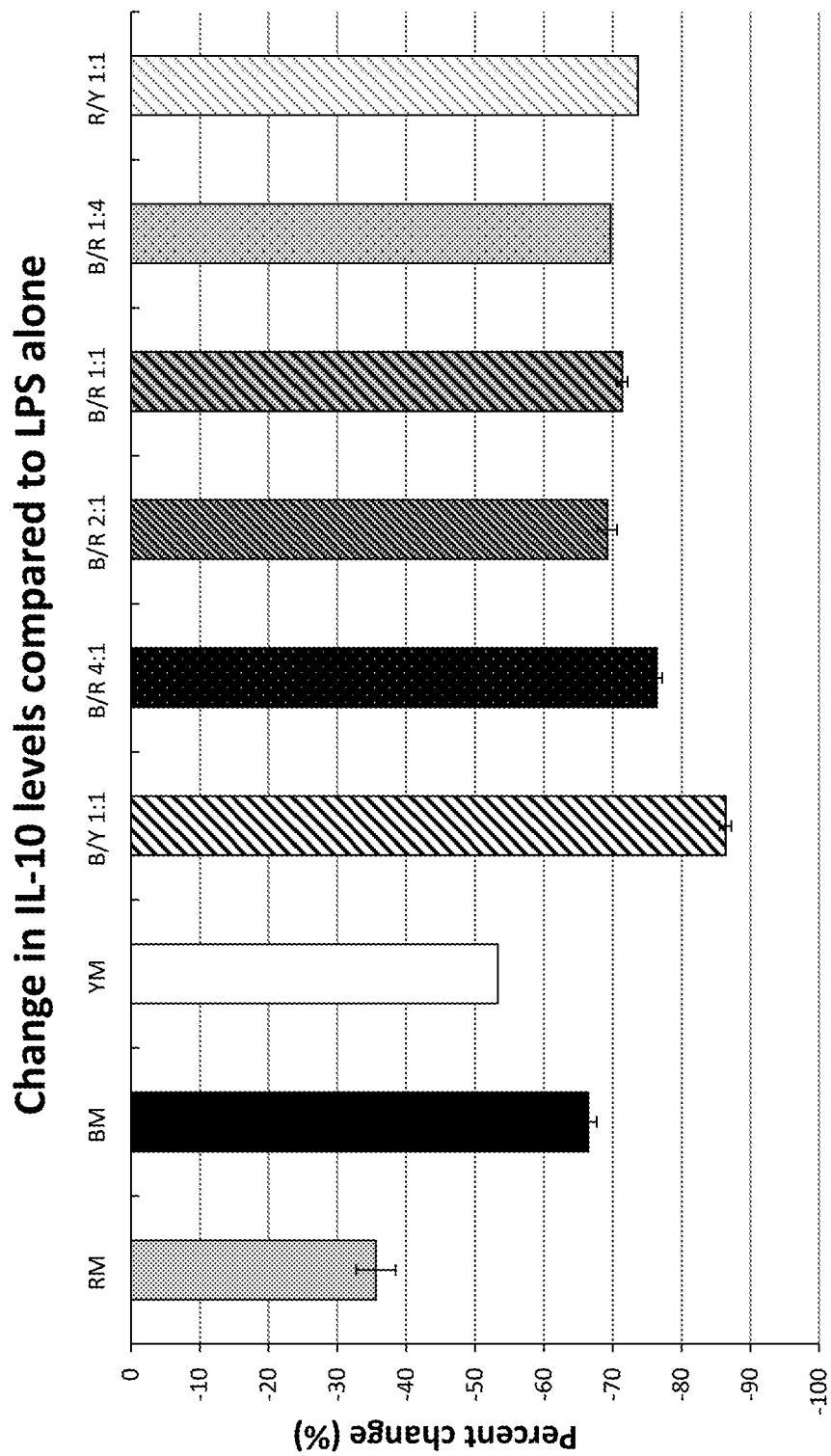
FIG. 5 represents the change in IL-10 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 5 represents the change in IL-10 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 6:
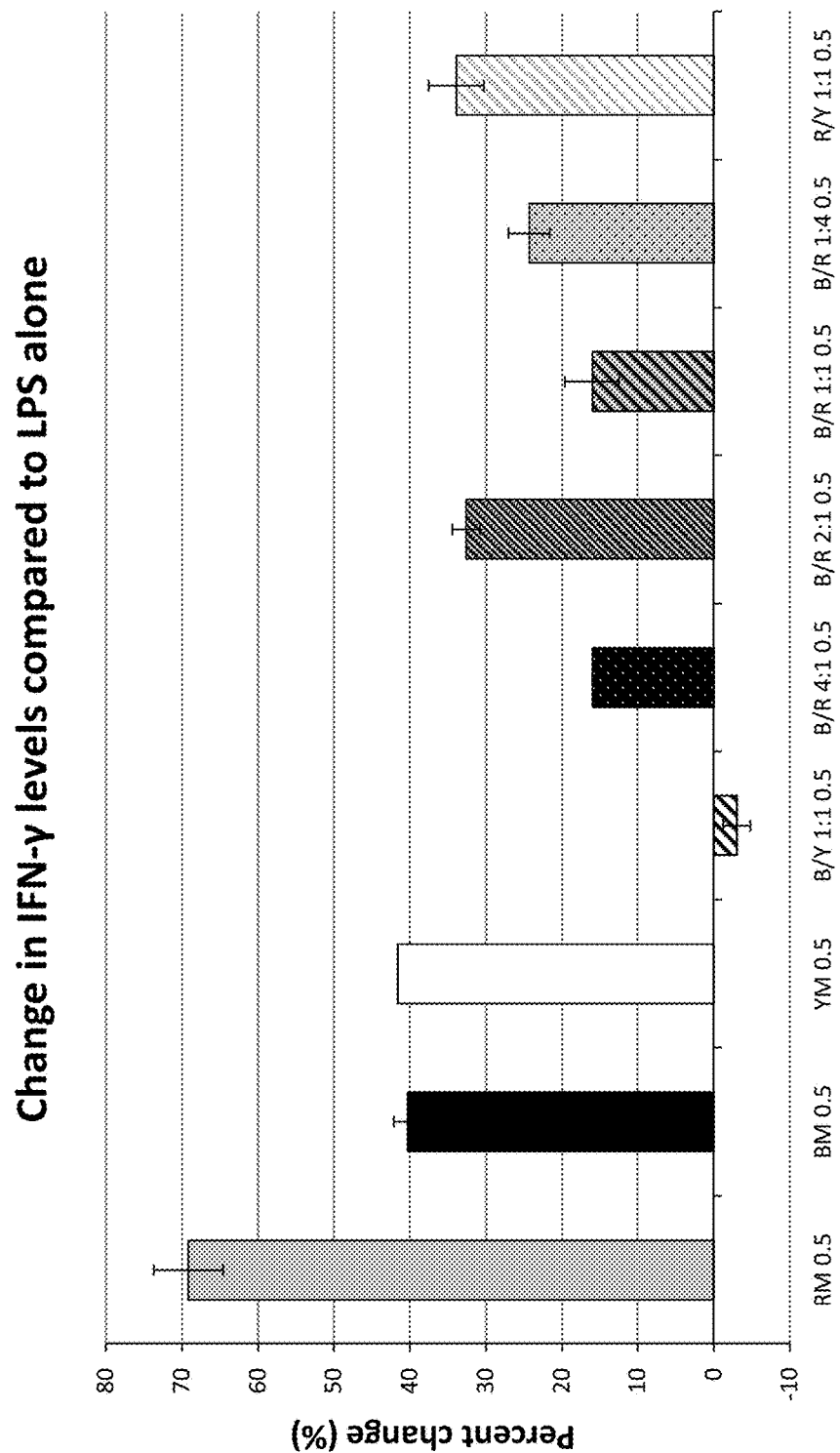
FIG. 6 represents the change in IFN-γ levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 6 represents the change in IFN-γ levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 7:
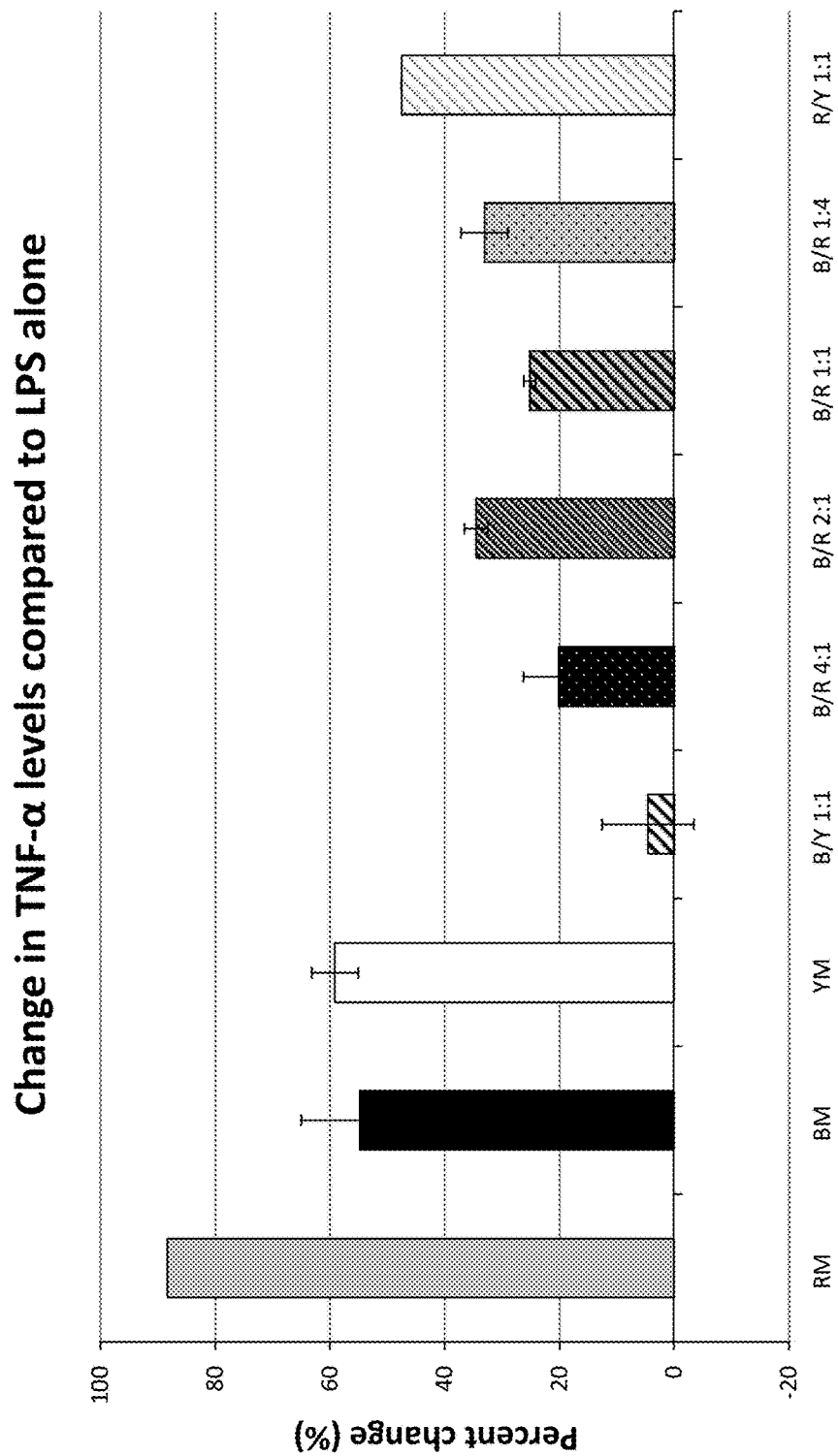
FIG. 7 represents the change in TNF-α levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 7 represents the change in TNF-α levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 8:
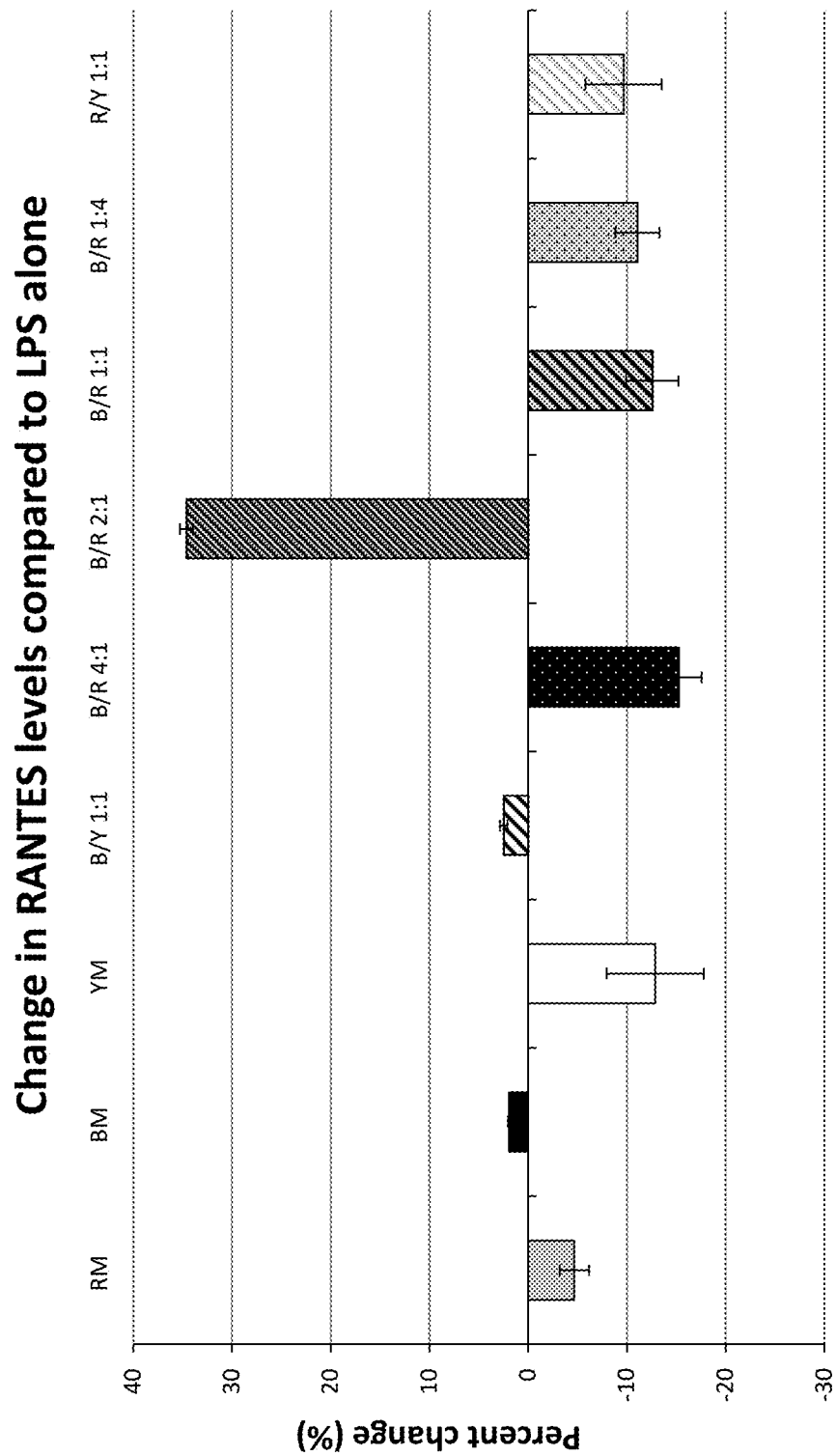
FIG. 8 represents the change in RANTES (regulated on activation, normal T-cell expressed and secreted) levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 8 represents the change in RANTES levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 9:
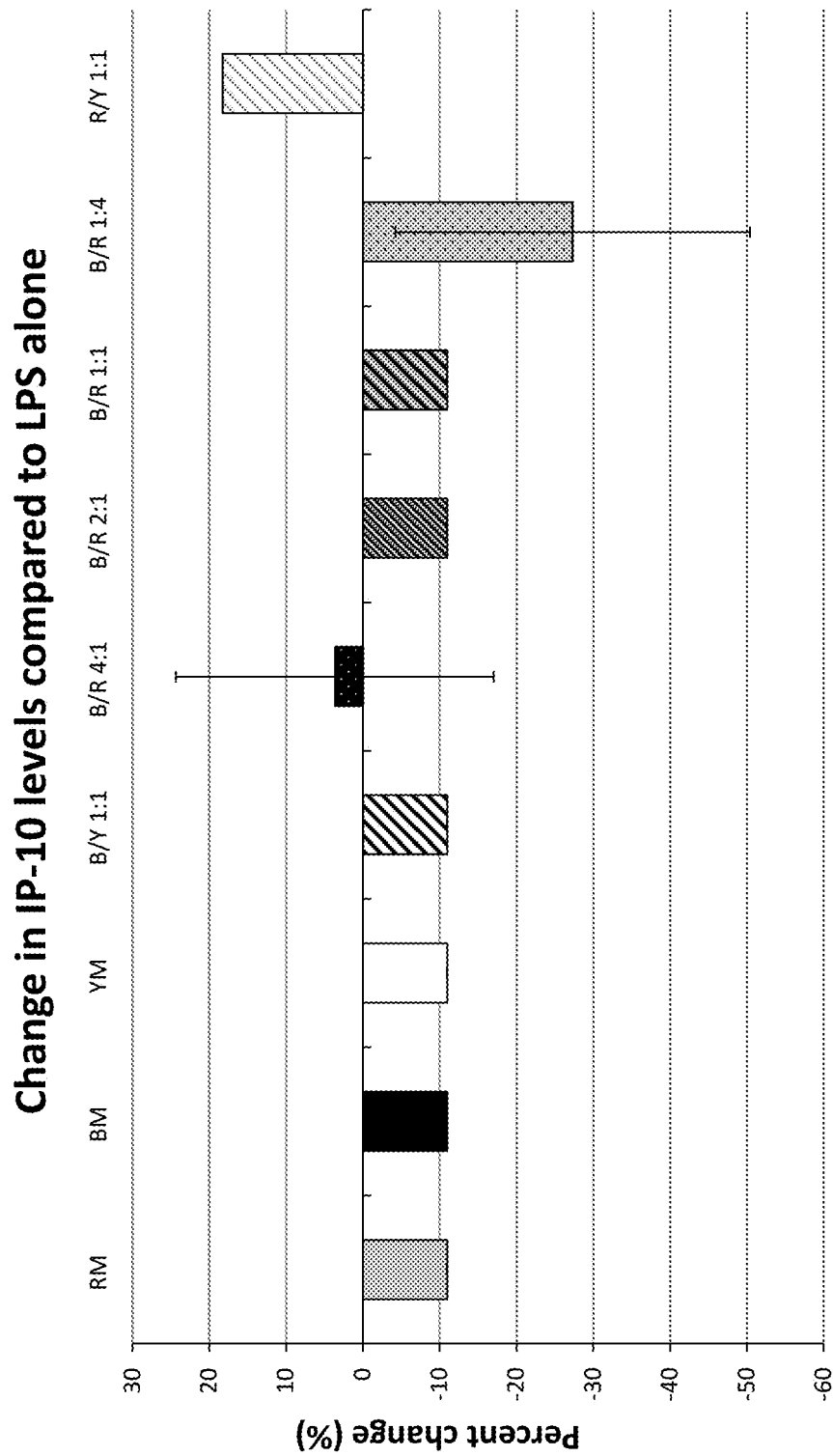
FIG. 9 represents the change in IP-10 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 9 represents the change in IP-10 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 10:
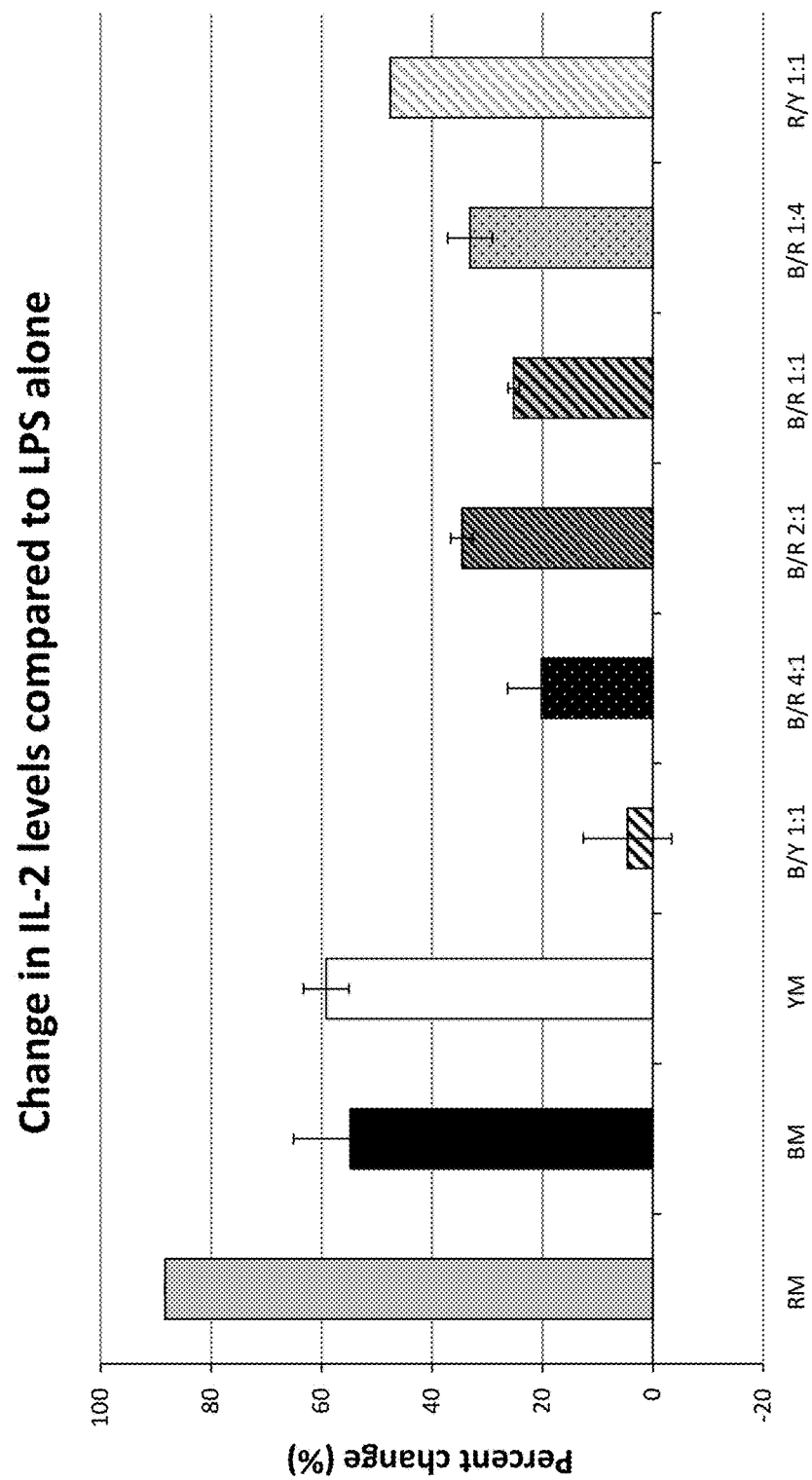
FIG. 10 represents the change in IL-2 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 10 represents the change in IL-2 levels in supernatants from PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

Figure 11:
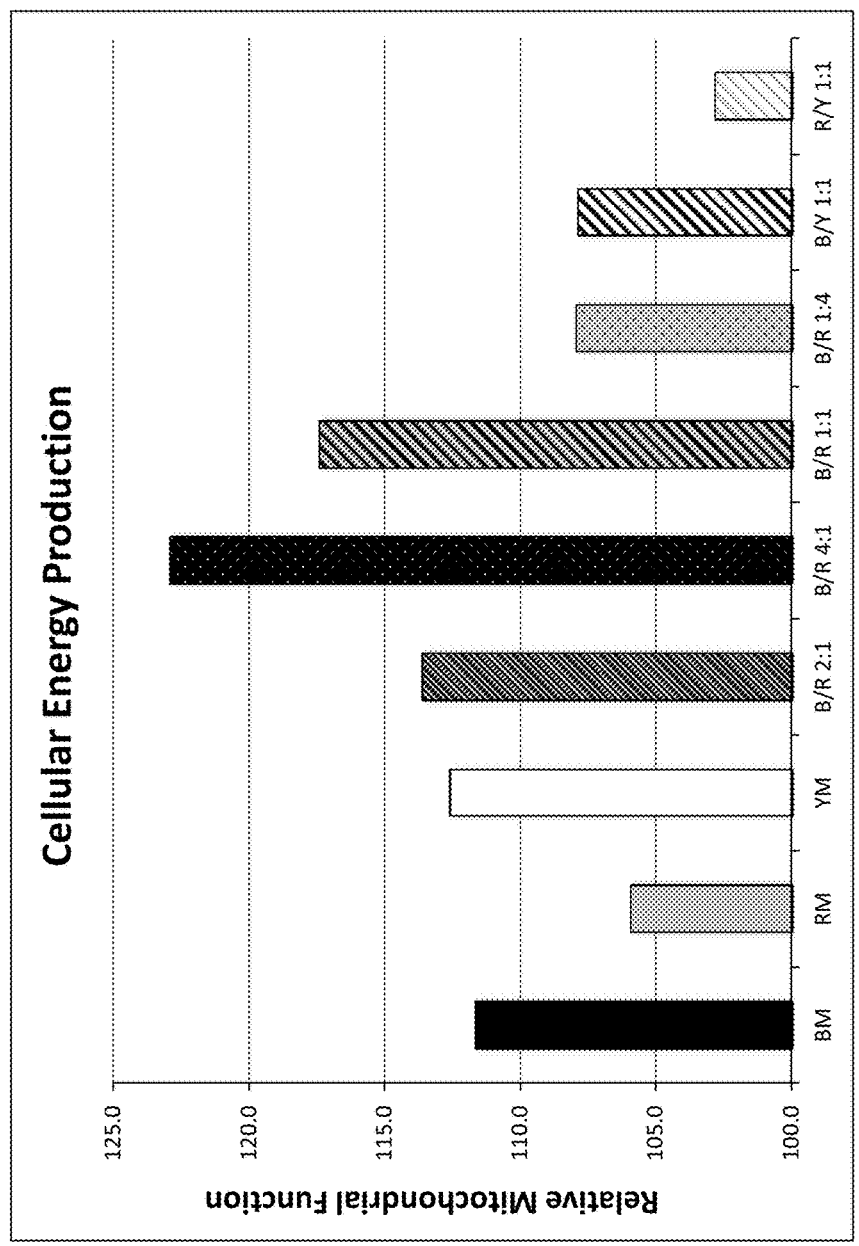
FIG. 11 represents the change in mitochondrial function in PBMC cultures treated with serial dilutions of test products for 24 hours in the presence of bacterial lipopolysaccharide (LPS). Data are shown as group averages plus or minus the standard deviation from each duplicate data set, when compared to the average cytokine production from cultures treated with LPS in the absence of test products.

FIG. 11 represents the change in mitochondrial function in PBMC cultures treated with serial dilutions of test products for 24 hours in the presence of bacterial lipopolysaccharide (LPS). These PBMC cultures were exposed to six 4-fold serial dilutions of each product, starting at 2 mg/mL. Testing conditions were performed in triplicate and cultures maintained at 37° C. and 5% $CO_2$ for 24 hours. After the 24-hour incubation, cultures were processed in the colorimetric MTT assay. An MTT assay utilizes a dye that changes color dependent on mitochondrial function, which is directly related to cellular metabolic activity and viability. Healthy cells metabolize the MTT dye and turn the cultures purple. When a reduction in color is measured, this is linked to reduced cellular viability, either as a result of direct killing, or inhibition of mitochondrial function leading to cell death. In this case, a measured increase in color is measured, which indicates an increased mitochondrial function (energy production) because unstimulated PBMC do not undergo cell division in the 24-hour period and the increased colorimetric reading observed in several maca-treated cell cultures are likely linked to direct effects on cellular energy production. Data are shown as group averages plus or minus the standard deviation from each duplicate data set, when compared to the average cytokine production from cultures treated with LPS in the absence of test products.

These results demonstrate that compositions comprising both 4:1 black maca root to red maca root and 1:1 black maca root to yellow maca root possess significant anti-inflammatory effects. For example, but not limited to, reduction of IL-6 (0.02 g), IL-8 (both 0.5 and 0.02 g/L), and reduction of IL-1β were all stronger than for either black or red maca root alone. Such results were not expected or predicted.

Example 2: Effects of Maca Compositions on Inflammation

A double-blind, randomized, parallel group dose-finding pilot study is conducted to compare a dose of an appropriate amount of a maca composition per day as a daily regimen to a placebo control in 40 outpatients (mean age 30; half females, half males) with diagnosed chronic inflammation and/or an autoimmune disease, disorder, or condition. The compositions may, for example, include a predetermined amount of maca per kg of a subjects' body weight. Subjects are required to have exhibited symptoms of chronic inflammation and/or an autoimmune disease, disorder, or condition for at least six months prior to initiating the trial, and may not have commenced any new medications within six months of initiating the trial.

The subjects are divided into groups of eight, Groups A, B, C, D, and E. Group A is the control group, Group B receives yellow maca only, Group C receives 1:1 black to red maca, Group D receives 4:1 black to red maca, and Group E receives 1:1 black to yellow maca. Blood samples are taken from each subject at week 0, week 1, week 4, week 8, week 12, and week 16. Cytokine levels are measured in each sample. At each blood draw, subjects also complete a brief questionnaire regarding their symptoms.

Subjects in each group report mild to moderate alleviation of symptoms, with subjects in Group B reporting similar results to control Group A. Subjects in Groups C, D, report the most improvement in symptoms relative to Groups A and B, with subjects in Group D reporting the greatest improvement. Similarly, Groups C and D also have the largest decrease in cytokine levels, particularly in IL-6 levels.

Example 3: Effects of Maca Compositions on Libido and Sexual Function

A double-blind, randomized, parallel group dose-finding pilot study is conducted to compare a dose of an appropriate amount of a maca composition per day as a daily regimen (relative to placebo control) in 40 outpatients (mean age 36; 17 females) with diagnosed sexual dysfunction. The compositions may, for example, include a predetermined amount of maca per kg of a subjects' body weight. Subjects are required to meet at least one of the following criteria for at least 4 weeks: (1) inability to have an orgasm (anorgasmia) during sexual activity; (2) clinically significant orgasm delay with masturbation or intercourse that, according to self-report, representing a meaningful delay and interfering with sexual function compared with the subject's usual time to achieve orgasm; (3) inability to attain or maintain until completion of sexual activity an adequate erection or lubrication swelling response of sexual excitement that, according to self-report, interfered with sexual function compared to prior to antidepressant medication; (4) decreased libido according to self-report.

Exclusion criteria include: primary or prior diagnosis of a sexual disorder; sexual dysfunction secondary to general underlying medical condition; no other current primary psychiatric disorder; alcohol or substance abuse or dependence within the past 6 months; recent major sexual relationship changes, disruption, or turmoil ongoing or anticipated which are unrelated to their sexual dysfunction, HAM-D-17 or HAM-A score (either) >10; current use of other drugs for sexual dysfunction or other therapies or medications to treat sexual dysfunction; hormone replacement therapy, unless patient had been on stable dose of hormone therapy for at least 3 months prior to the antidepressant treatment, had no sexual dysfunction while on the same hormone therapy regimen, and there was no change in the hormone replacement therapy during the study; pregnancy, lactation, or plans to become pregnant during the study; any clinically significant abnormality of the screening physical examination; any medical or psychological condition or social circumstances that would impair subject's ability to participate reliably in the study, or that may have increased the risk to subjects or others as a result of participating in the study; testosterone implant during 6 months prior to screening; receiving psychosexual or other therapy for sexual dysfunction and not willing to discontinue that treatment at screening; and/or subjects for whom sexual activity was inadvisable.

The subjects are divided into groups of eight, Groups A, B, C, D, and E. Group A is the control group, Group B receives yellow maca only, Group C receives 1:1 black to red maca, Group D receives 4:1 black to red maca, and Group E receives 1:1 black to yellow maca. The Arizona Sexual Experience Scale (ASEX) and the Massachusetts General Hospital Sexual Function Questionnaire (MGH-SFQ) are used to measure sexual dysfunction. Subjects in Group B report similar results to control Group A. Subjects in Groups C, D, report improved sexual function and libido relative to Groups A and B, with subjects in Group D reporting the greatest improvement.

Example 4—Reduction of Fatigue and Improvement of Metabolic Activity

Rats were randomly divided into 4 groups with similar body weight as follows: 1) control group (vehicle); 2) maca powder (40 mg/kg body weight), 3) Exercise; 4) Exercise+ Maca powder (40 mg/kg body weight) where the groups administered a maca composition as described herein were given a maca composition comprising black and red maca at a ratio of 4:1. The control groups were treated with a similar volume of vehicle without any maca. Those groups receiving doses of maca powder received the maca powder intragastrically in a volume of 0.2 g/10 mL once per day for 21 consecutive days. The control group were treated with a similar volume of vehicle without any maca powder.

Rats were made to swim without loading for 10 min, twice a week, to accustom them to swimming. On the 14th day of the experiment, the weight-loaded swimming test was employed to evaluate the effects of maca powder on the endurance capacity of mice along with determining the effect on certain indicators related to physical exertion. 30 minutes after the oral administration of maca powder or vehicle without maca powder, the rats were dropped individually into an acrylic plastic pool containing fresh water maintained at 27±1° C., approximately 35 centimeters deep. The rats were loaded with a lead block, weighing approximately 5% of their body weight, attached to the tail. The swimming time to exhaustion was used as one index of the degree of fatigue. The rats were considered to be exhausted when they could not keep their nose out of the water within a 10 second period.

After the weight-loaded swimming test, the control and test rats were orally administered for 7 more days with vehicle containing no maca and vehicle with the maca root composition, respectively. Thirty minutes after the last dosing on the 21st day, each rat was sacrificed immediately after 90 minutes swimming without load. The selection of swimming time that leads to fatigue was according to methods known in the prior art. Blood, liver, muscle and brain samples were collected. The levels of serum glucose, lactate (LD), lactate dehydrogenase (LDH), blood urea nitrogen (BUN), and the contents of liver glycogen was measured using commercially available kits according to the manufacturer's instructions.

Immediately after the blood was collected, the brain, liver, and left gastrocnemius muscle was quickly dissected out, and kept at −80° C. until analysis. Each tissue was homogenized in ice-cold normal saline. These tissue homogenates were centrifuged at 3000 rpm for 10 min at 4° C., and the supernatants were assessed for the antioxidant status.

The activities of superoxide dismutase (SOD) and glutathione peroxidase (GSH-PX), the contents of lipid peroxidation product malondialdehyde (MDA), were determined using commercially available kits according to the manufacturer's protocol. SIRT1, mitochondrial transcription factor A (TFAM), NF-kB, and Nrf2 were analyzed by Western blot methods in muscle samples using methods known in the art.

TABLE 3

Experimental protocol

| Group I, N = 7/arm | Group II, N = 7/arm |
|---|---|
| Control | Exercise |
| Control + Maca Powder | Exercise + Maca Powder |

Table 3 above presents the experimental protocol that was utilized. The following table summarizes the experimental results that were obtained.

treatment was used. The data was analyzed using the GLM procedure of SAS (SAS Institute: SAS User's Guide: Statistics), which is known to one of skill in the art. The treatments were compared using ANOVA and student's unpaired t test; $P<0.05$ was considered statistically significant.

Figure 12:
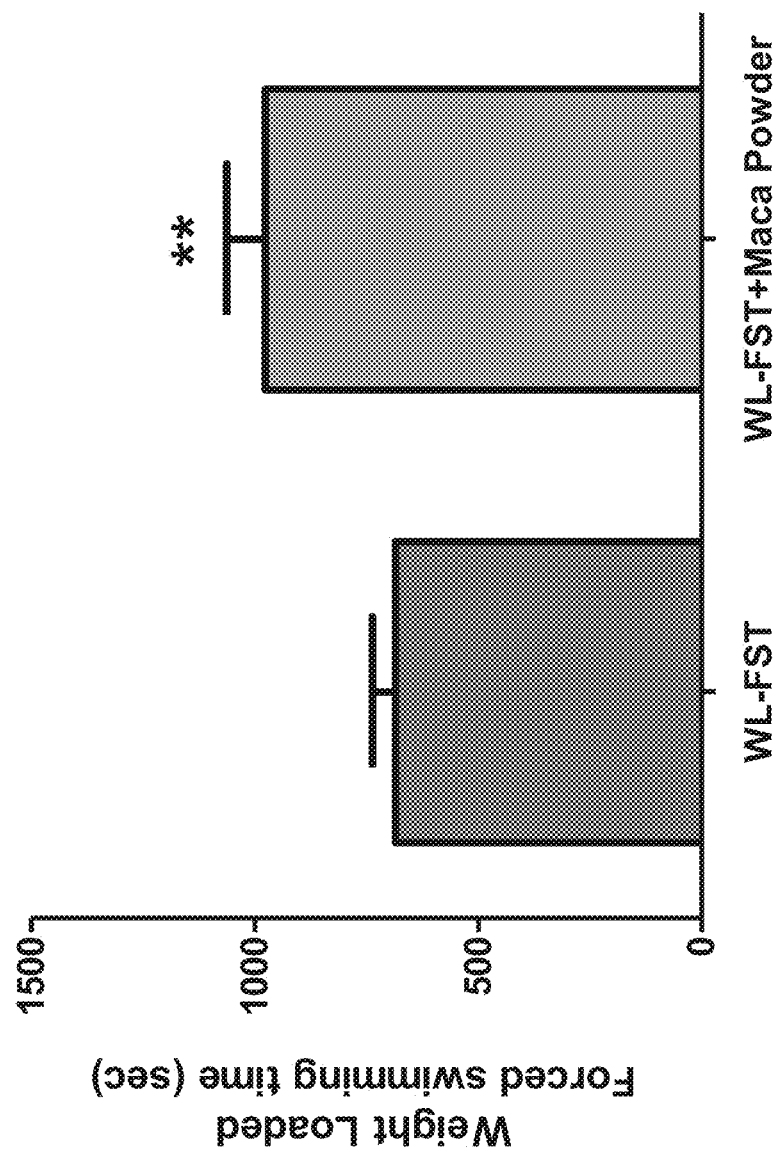
FIG. 12 represents the increase in forced swimming time achieved by rats subject to the protocol of Example 4. An increased forced swimming time was measured after administration of a maca composition comprising black maca and red maca wherein the black maca and red maca were present in a ratio of 4:1.

FIG. 12 represents the increase in forced swimming time achieved by rats subject to the protocol of Example 4. An increased forced swimming time was measured after administration of a maca composition comprising black maca and red maca wherein the black maca and red maca were present in a ratio of 4:1.

Figure 13:
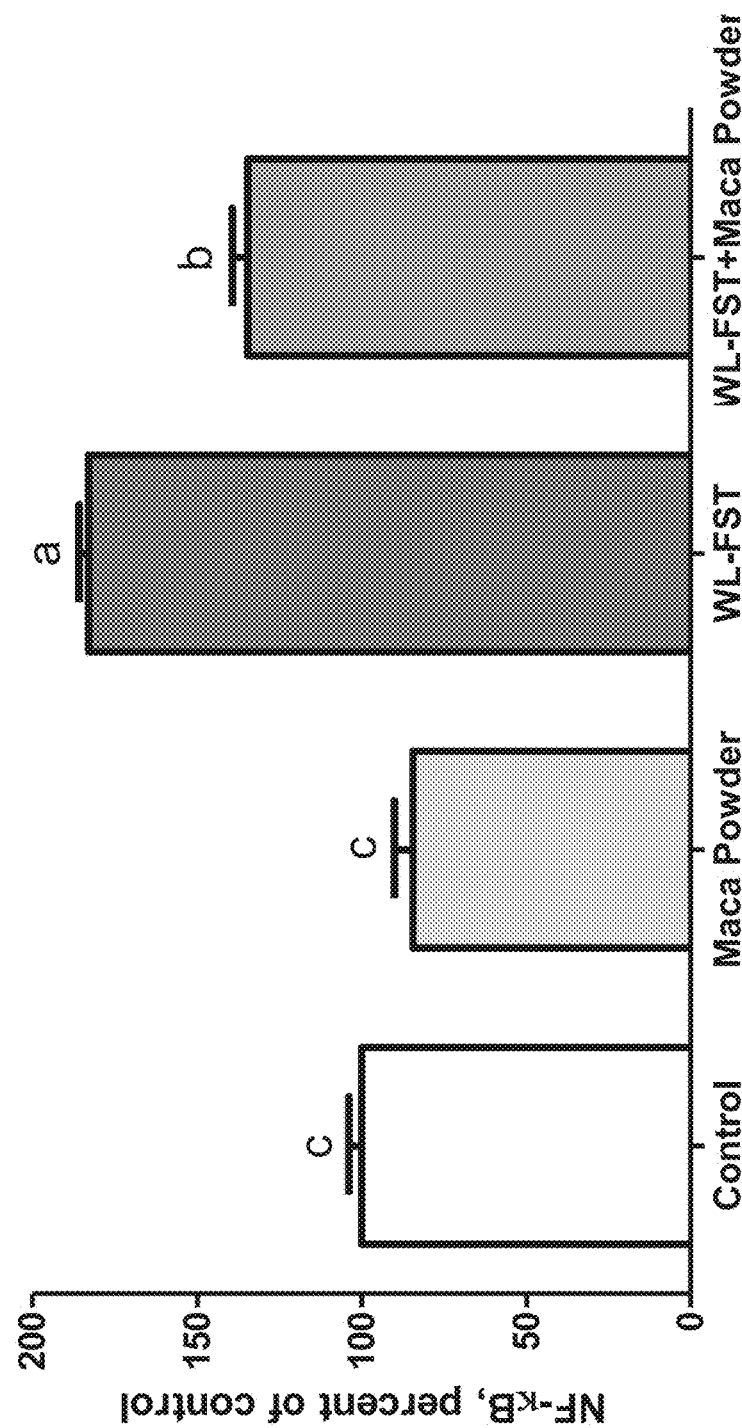
FIG. 13 represents the decrease in NF-κB measured in rats in the protocol of Example 4. A decrease in NF-κB was measured after administration of a maca composition comprising black maca and red maca wherein the black maca and red maca were present in a ratio of 4:1.

FIG. 13 represents the decrease in NF-κB measured in rats in the protocol of Example 4. A decrease in NF-κB was measured after administration of a maca composition comprising black maca and red maca wherein the black maca and red maca were present in a ratio of 4:1.

Figure 14:
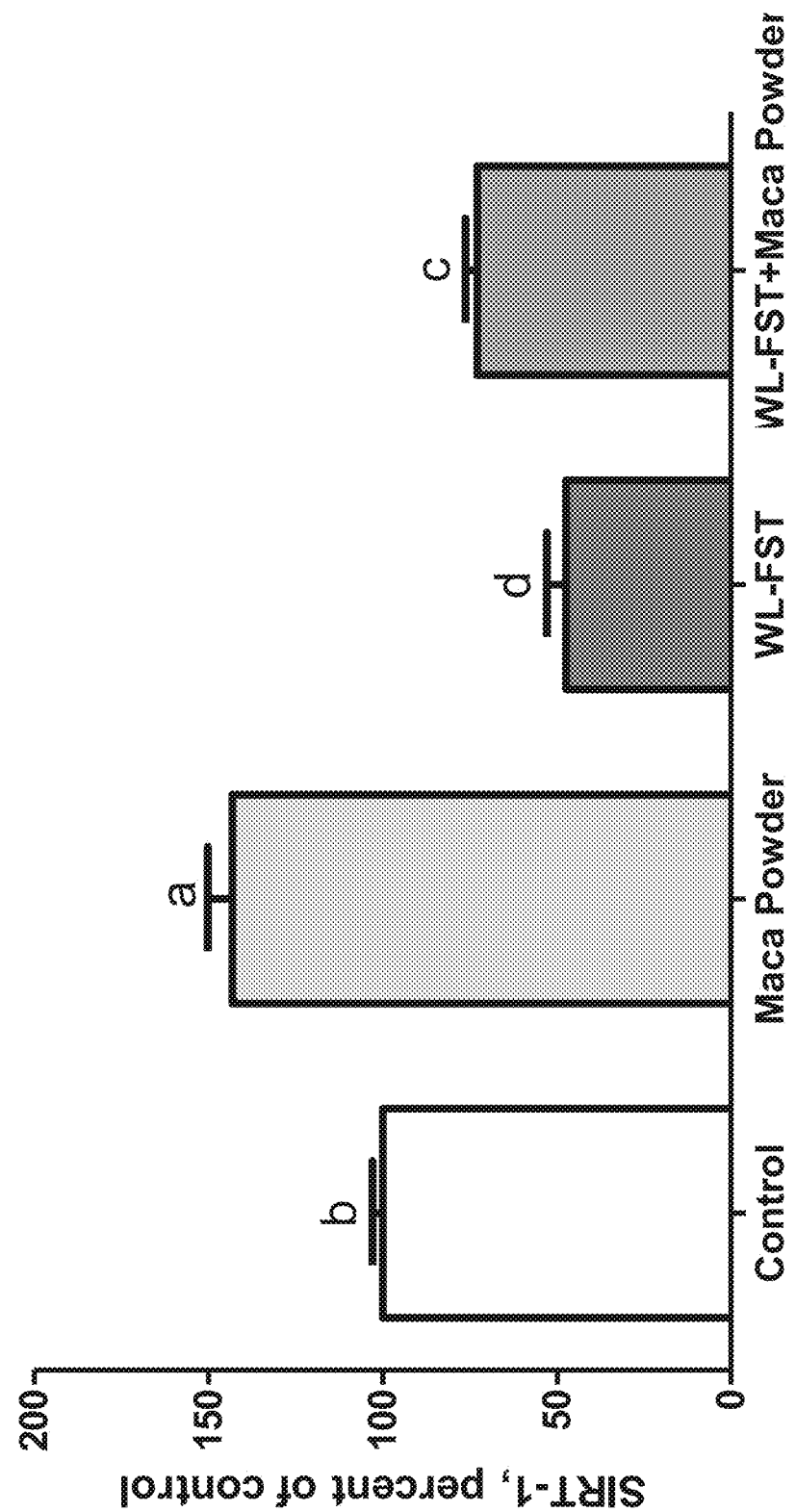
FIG. 14 represents the increase of SIRT-1 measured in rats in the protocol of Example 4. An increase in SIRT-1 was measured after administration of a maca composition comprising black maca and red maca wherein the black maca and red maca were present in a ratio of 4:1.

FIG. 14 represents the increase of SIRT-1 measured in rats in the protocol of Example 4. An increase in SIRT-1 was measured after administration of a maca composition comprising black maca and red maca wherein the black maca and red maca were present in a ratio of 4:1.

Figure 15:
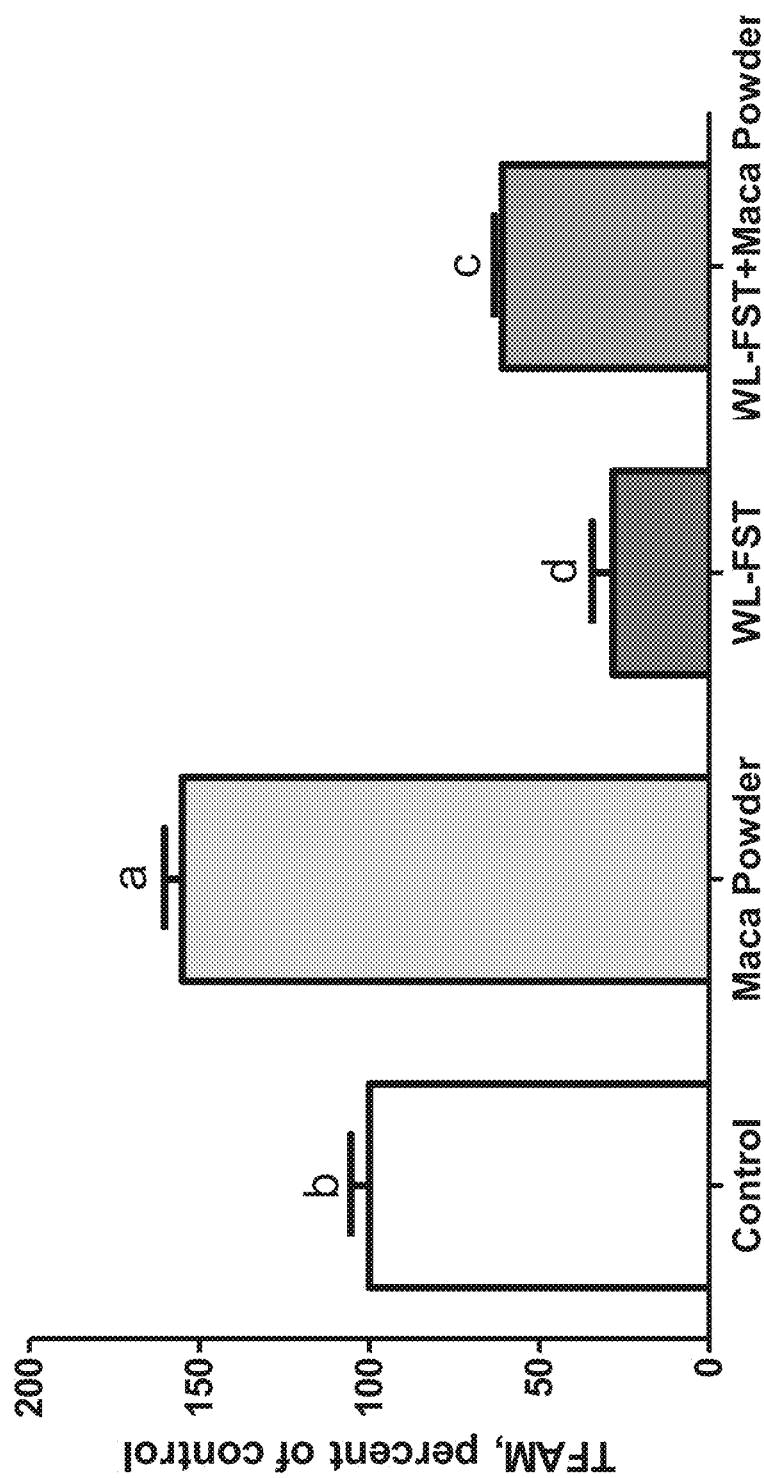
FIG. 15 represents the increase of mitochondrial transcription factor A (TFAM) measured in the rats in the protocol of Example 4. An increase in TFAM was measured after administration of a maca composition comprising black maca and red maca wherein the black maca and red maca were present in a ratio of 4:1.

FIG. 15 represents the increase of mitochondrial transcription factor A (TFAM) measured in the rats in the protocol of Example 4. An increase in TFAM was measured after administration of a maca composition comprising black maca and red maca wherein the black maca and red maca were present in a ratio of 4:1.

Figure 16:
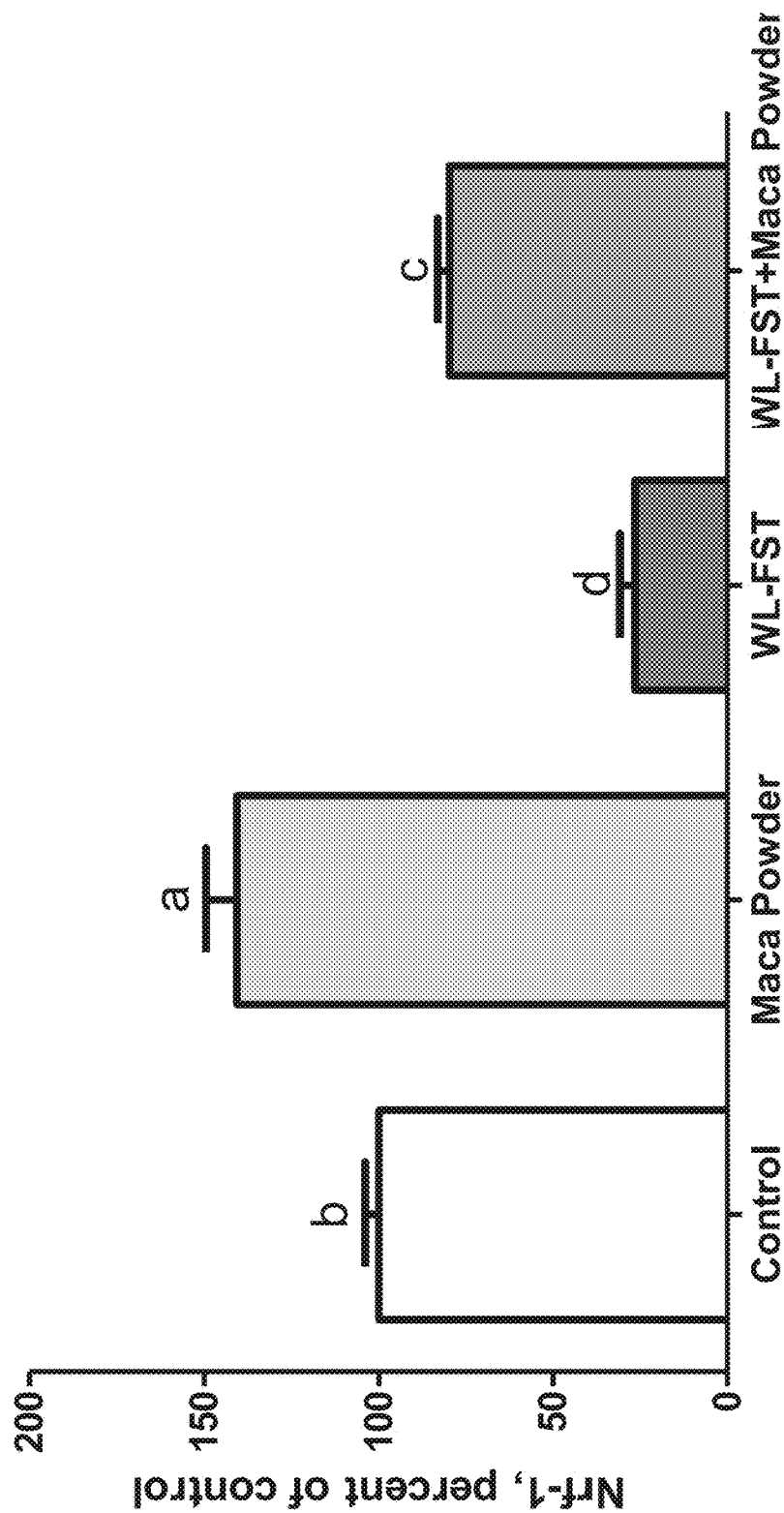
FIG. 16 represents the increase of nuclear respiratory factor 1 (Nrf-1) measured in the rats in the protocol of Example 4. An increase in Nrf-1 was measured after administration of a maca composition comprising black maca and red maca wherein the black maca and red maca were present in a ratio of 4:1.

FIG. 16 represents the increase of nuclear respiratory factor 1 (Nrf-1) measured in the rats in the protocol of Example 4. An increase in Nrf-1 was measured after admin-

TABLE 4

Experimental results obtained with administration of a black:red maca composition with a ratio of 4:1.

| | Groups | | | | |
|---|---|---|---|---|---|
| Items | Control | Maca Powder | WL-FST | WL-FST + Maca Powder | --P-- |
| Initial BW, g | 271.71 ± 4.05 | 272.43 ± 3.32 | 271.43 ± 5.26 | 273.00 ± 2.06 | 0.991 |
| Final BW, g | 287.86 ± 6.21$^{ab}$ | 291.57 ± 3.41$^a$ | 269.00 ± 4.99$^b$ | 275.57 ± 6.54$^{ab}$ | 0.024 |
| Glucose, mg/dL | 94.29 ± 1.92$^{bc}$ | 86.86 ± 1.97$^c$ | 109.57 ± 3.29$^a$ | 103.43 ± 2.59$^{ab}$ | 0.0001 |
| Lactate mg/dL | 7.31 ± 0.53$^c$ | 7.57 ± 0.36$^c$ | 21.89 ± 1.36$^a$ | 12.74 ± 1.07$^b$ | 0.0001 |
| Creatine, mg/dL | 0.44 ± 0.05 | 0.48 ± 0.06 | 0.52 ± 0.07 | 0.58 ± 0.17 | 0.771 |
| BUN, mg/dL | 7.71 ± 0.54 | 7.61 ± 0.34 | 7.79 ± 0.32 | 7.97 ± 0.44 | 0.941 |
| ALT, U/L | 78.29 ± 3.26 | 75.43 ± 2.42 | 77.57 ± 2.55 | 76.71 ± 3.62 | 0.917 |
| AST, U/L | 112.43 ± 6.98 | 109.57 ± 6.83 | 117.43 ± 7.26 | 111.71 ± 4.26 | 0.849 |
| T-C, mg/dL | 53.43 ± 3.15 | 50.14 ± 6.50 | 54.14 ± 2.98 | 51.29 ± 2.33 | 0.890 |
| TG, mg/dL | 60.86 ± 5.15 | 57.57 ± 4.53 | 59.43 ± 4.01 | 58.43 ± 2.33 | 0.950 |
| Liver Glycogen, mg/g | 20.43 ± 2.21$^a$ | 15.99 ± 1.33$^{ab}$ | 17.31 ± 1.45$^{ab}$ | 11.34 ± 1.19$^b$ | 0.005 |
| Serum MDA, μmol/L | 0.71 ± 0.03$^c$ | 0.44 ± 0.04$^d$ | 1.60 ± 0.06$^a$ | 1.17 ± 0.04$^b$ | 0.0001 |
| Muscle MDA, nmol/g | 1.57 ± 0.06$^c$ | 1.18 ± 0.05$^d$ | 2.53 ± 0.06$^a$ | 2.04 ± 0.05$^b$ | 0.0001 |
| Liver MDA, nmol/g | 2.10 ± 0.11$^c$ | 1.64 ± 0.06$^d$ | 3.28 ± 0.10$^a$ | 2.52 ± 0.12$^b$ | 0.0001 |
| Liver SOD | 85.64 ± 2.46$^{ab}$ | 91.47 ± 2.29$^a$ | 71.02 ± 2.08$^c$ | 78.22 ± 2.58$^{bc}$ | 0.0001 |
| Muscle SOD | 79.40 ± 1.74$^{ab}$ | 84.89 ± 2.76$^a$ | 71.64 ± 1.14$^b$ | 75.79 ± 2.32$^b$ | 0.001 |
| Liver GSH-Px | 116.32 ± 2.28$^b$ | 120.93 ± 2.09$^a$ | 106.57 ± 2.06$^b$ | 113.08 ± 2.40$^{ab}$ | 0.001 |
| Muscle GSH-Px | 11.10 ± 0.38$^b$ | 14.08 ± 0.38$^a$ | 6.26 ± 0.11$^d$ | 8.99 ± 0.25$^c$ | 0.0001 |

BW: Body weight; BUN: Blood urea nitrogen; ALT: Alanine aminotransferase; AST: Aspartate aminotransferase; T-C: Total Cholesterol; TG: Triglycerides; Data are means ± SE. Different superscripts (a-d) indicate group mean differences (p < 0.05).
WL: Weight loaded; FST: Forced swimming test; MDA: Malondialdehyde; SOD: Superoxide dismutase; GSH-Px: glutathioneperoxidase.). WL: Weight loaded; FST: Forced swimming test
Data are means ± SE. Different superscripts (a-d) indicate group mean differences (p < 0.05).

The data in table 4 is given as mean±SEM. Sample size was calculated based on a power of 85% and a p value of 0.05. Given that assumption, a sample size of seven per istration of a maca composition comprising black maca and red maca wherein the black maca and red maca were present in a ratio of 4:1.

Figure 17:
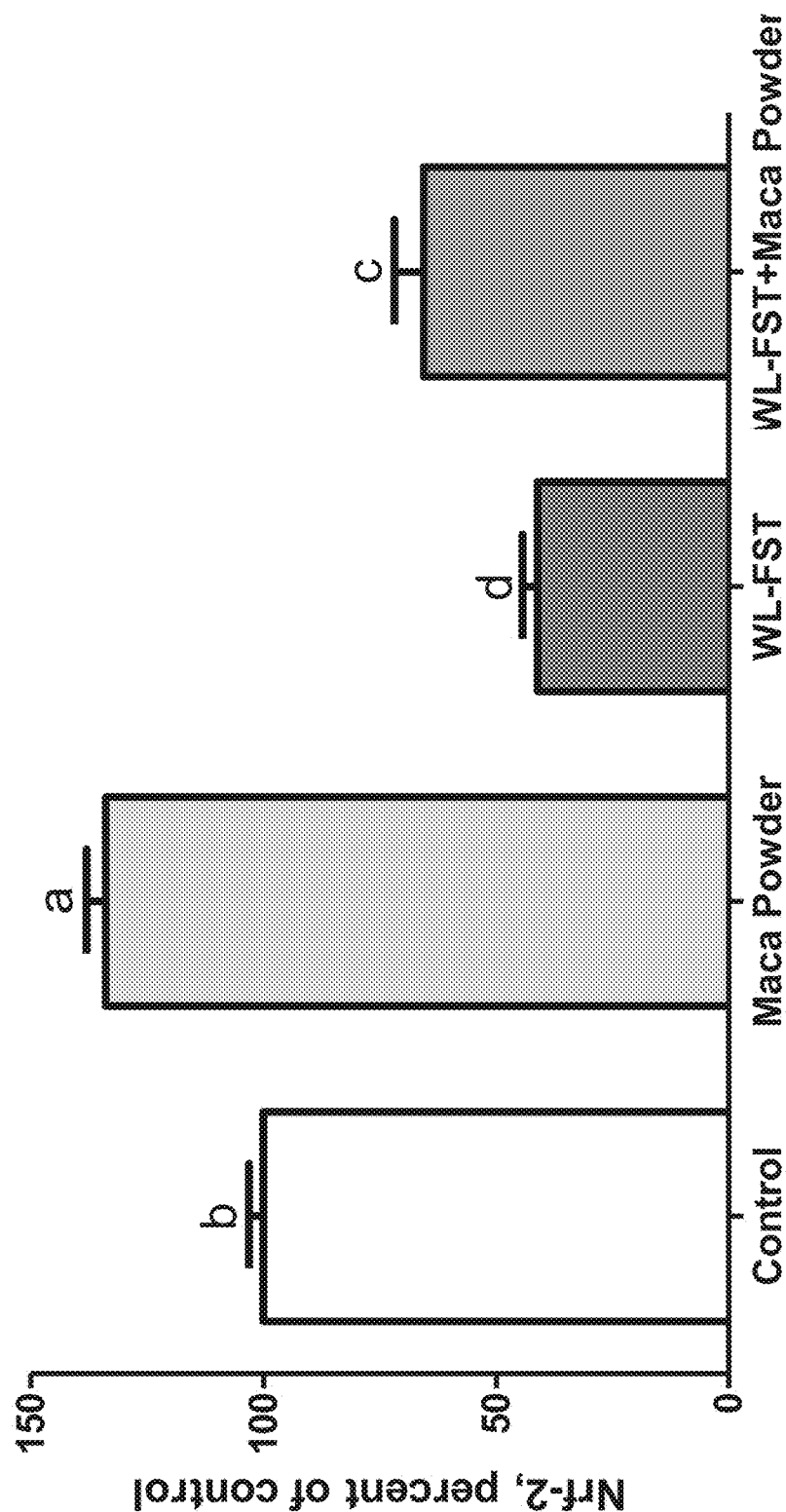
FIG. 17 represents the increase of nuclear factor erythroid 2 (Nrf-2) measured in the rats in the protocol of Example 4. An increase in Nrf-2 was measured after administration of a maca composition comprising black maca and red maca wherein the black maca and red maca were present in a ratio of 4:1.

FIG. 17 represents the increase of nuclear factor erythroid 2 (Nrf-2) measured in the rats in the protocol of Example 4. An increase in Nrf-2 was measured after administration of a maca composition comprising black maca and red maca wherein the black maca and red maca were present in a ratio of 4:1.

Figure 18:
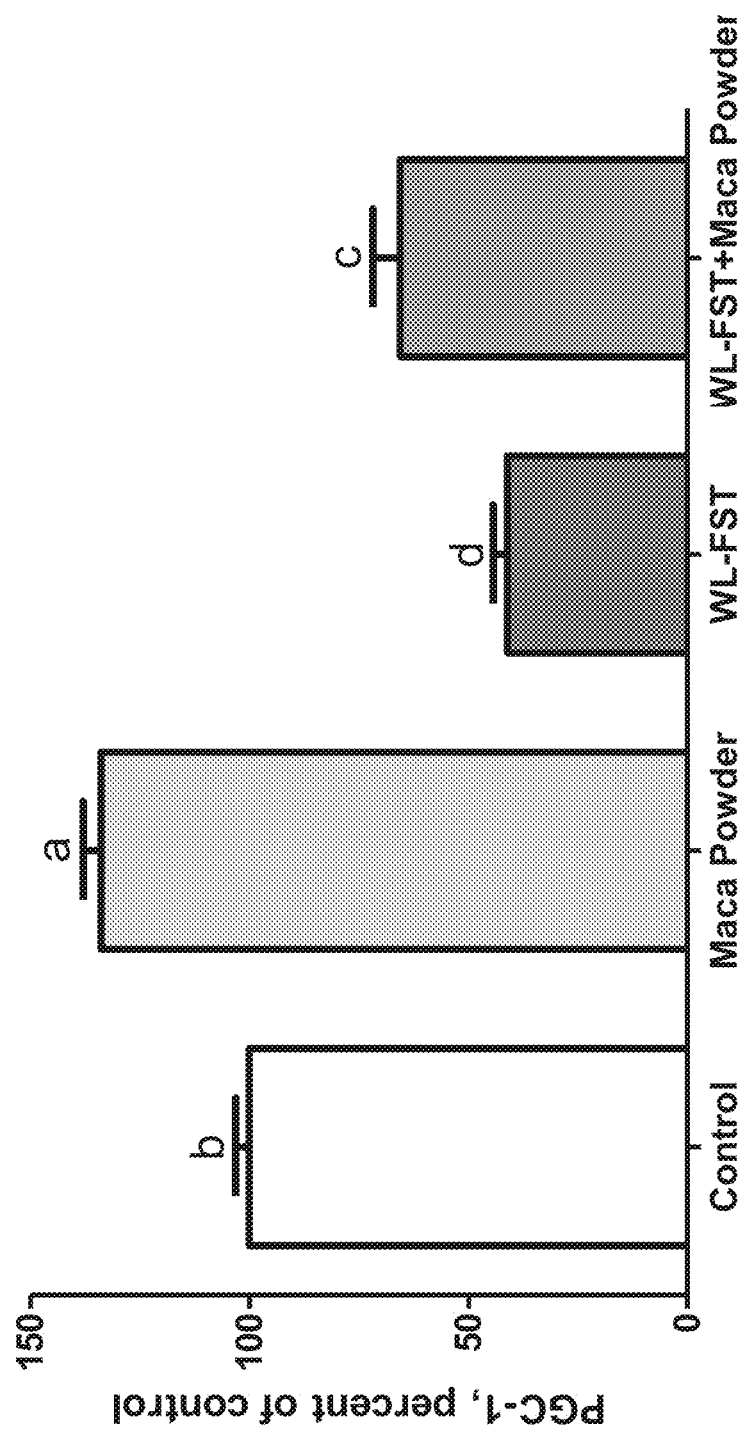
FIG. 18 represents the increase of peroxisome proliferator-activated receptor-gamma coactivator (PGC-1) measured in the rats in the protocol of Example 4. An increase in PGC-1 activity was measured after administration of a maca composition comprising black maca and red maca wherein the black maca and red maca were present in a ratio of 4:1.

FIG. 18 represents the increase of peroxisome proliferator-activated receptor-gamma coactivator (PGC-1) measured in the rats in the protocol of Example 4. An increase in PGC-1 activity was measured after administration of a maca composition comprising black maca and red maca wherein the black maca and red maca were present in a ratio of 4:1.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications can be made to the invention disclosed herein without departing from the scope and spirit of the invention.

As used in the claims below and throughout this disclosure, by the phrase "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. A nutritional supplement comprising:
   an effective amount of a maca composition (*Lepidium mevenii*), wherein the maca composition consists of a synergistic combination of black maca and red maca in a ratio of about 4:1;
   wherein the maca composition has between about 15 and 40 grams of total sugar per 100 grains of the maca composition;
   wherein the maca composition has between about 250 and 450 milligrams of total polyphenols per 100 grams of the maca composition; and
   wherein the nutritional supplement is provided in a dosage form wherein the dosage form is selected from the group consisting of a tablet, a dispersible powder or granule, emulsion, hard capsule, or soft capsule.

2. The nutritional supplement of claim 1, wherein the nutritional supplement is used for improving mitochondrial function.

3. The nutritional supplement of claim 1, wherein the nutritional supplement is used for increasing cellular energy.

4. The nutritional supplement of claim 1, wherein the nutritional supplement is used for reducing fatigue.

5. The nutritional supplement of claim 1, wherein the nutritional supplement is used for increasing physical stamina.

6. The nutritional supplement of claim 1, wherein the nutritional supplement is used for increasing anaerobic working capacity.

7. The nutritional supplement of claim 1, wherein the nutritional supplement is used for reducing lactate formation.

8. The nutritional supplement of claim 1, wherein the nutritional supplement has a pH of less than 5.4.

* * * * *